United States Patent
Zhang et al.

(10) Patent No.: US 11,590,241 B2
(45) Date of Patent: *Feb. 28, 2023

(54) NANOPARTICLE CONJUGATED SYNTHETIC OPIOID PRODRUGS AND METHODS OF THEIR USES

(71) Applicant: VIRGINIA COMMONWEALTH UNIVERSITY, Richmond, VA (US)

(72) Inventors: Yan Zhang, Glen Allen, VA (US); Hu Yang, Richmond, VA (US); Dana Selley, Richmond (VA); William Dewey, Richmond, VA (US); Hamid Akbarali, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1062 days.

This patent is subject to a terminal disclaimer.

(21) Appl. No.: 15/998,948

(22) PCT Filed: Feb. 17, 2017

(86) PCT No.: PCT/US2017/018275
§ 371 (c)(1),
(2) Date: Aug. 17, 2018

(87) PCT Pub. No.: WO2017/143126
PCT Pub. Date: Aug. 24, 2017

(65) Prior Publication Data
US 2021/0205472 A1   Jul. 8, 2021

Related U.S. Application Data

(60) Provisional application No. 62/296,671, filed on Feb. 18, 2016.

(51) Int. Cl.
*A61K 47/69* (2017.01)
*A61K 31/485* (2006.01)
(Continued)

(52) U.S. Cl.
CPC ........ *A61K 47/6935* (2017.08); *A61K 31/485* (2013.01); *A61K 47/6907* (2017.08);
(Continued)

(58) Field of Classification Search
None
See application file for complete search history.

(56) References Cited

U.S. PATENT DOCUMENTS

2006/0105046 A1   5/2006 Bentley et al.
2009/0306228 A1   12/2009 Mickle et al.
(Continued)

FOREIGN PATENT DOCUMENTS

WO   WO-2014036566 A1 * 3/2014 ............ C08G 65/18

OTHER PUBLICATIONS

Xiong F, Xiong C, Yao J, Chen X, Gu N. Preparation, characterization and evaluation of breviscapine lipid emulsions coated with monooleate-PEG-COOH. International journal of pharmaceutics. Dec. 15, 2011;421(2):275-82. (Year: 2011).*
(Continued)

*Primary Examiner* — Nissa M Westerberg
(74) *Attorney, Agent, or Firm* — WCF IP

(57) ABSTRACT

Provided herein are nanoparticle conjugated synthetic opioid prodrugs that target the peripheral mu opioid receptor (MOR). The prodrugs exhibit long-lived bioavailability, do not compromise the analgesic effects of opioids administered for pain relief (and in some cases can be used for pain relief), and do not induce opioid withdrawal symptoms, when their use is discontinued. Certain of the prodrugs are especially useful for the prevention and/or treatment of unwanted opioid-induced side effects such as opioid-induced constipation (OIC).

4 Claims, 6 Drawing Sheets

P(EAMO)-NAP-PEG

(51) Int. Cl.
*A61P 25/04* (2006.01)
*A61P 1/00* (2006.01)
*B82Y 5/00* (2011.01)
*B82Y 30/00* (2011.01)
*B82Y 40/00* (2011.01)

(52) U.S. Cl.
CPC ............ *B82Y 5/00* (2013.01); *B82Y 30/00* (2013.01); *B82Y 40/00* (2013.01)

(56) References Cited

U.S. PATENT DOCUMENTS

| | | |
|---|---|---|
| 2010/0160299 A1 | 6/2010 | Baker et al. |
| 2014/0371255 A1 | 12/2014 | Zhang et al. |
| 2015/0258204 A1 | 9/2015 | Yang et al. |

OTHER PUBLICATIONS

Bennet et al.: "Biodegradable polymeric prodrugs of naltrexone", Journal of Controlled Release, vol. 16, No. 1-2, pp. 43-52, Jun. 1, 1991.

Lee et al.: "Naltrexone for the treatment of obesity: review and update", Expert Opinion on Pharmacotherapy, vol. 10, No. 11, pp. 1841-1845, Jun. 18, 2009.

Xu et al: "Nanoconjugated NAP as a Potent and Periphery Selective Mu Opioid Receptor Modulator to Treat Opioid-Induced Constipation", ACS Medicinal Chemistry Letters, vol. 8, No. 1, pp. 78-83, Nov. 23, 2016.

Zhang et al: "Opioid receptor selectivity profile change via isosterism for 14-0-substituted naltrexone derivatives", Bioorganic & Medicinal Chemistry Letters, vol. 23, No. 13, pp. 3719-3722, May 16, 2013.

Abeylath et al., "'Click' Synthesis of Dextran Macrostructures for Combinatorial-Designed Self-Assembled Nanoparticles Encapsulating Diverse Anticancer therapeutics", Bioorg Med Chem. 2011, vol. 19(21), pp. 6167-6173.

\* cited by examiner

NANOPARTICLE CONJUGATED SYNTHETIC OPIOID PRODRUGS AND METHODS OF THEIR USES

CROSS-REFERENCE TO RELATED APPLICATIONS

This application claims benefit of U.S. provisional patent application 62/296,671, filed Feb. 18, 2016, the complete contents of which is hereby incorporated by reference.

STATEMENT OF FEDERALLY SPONSORED RESEARCH AND DEVELOPMENT

This invention was made with government support under grant #DA024022 awarded by the National Institutes of Health. The United States government has certain rights in the invention.

BACKGROUND OF THE INVENTION

Field of the Invention

The invention generally relates to synthetic opioid prodrugs. In particular, the invention provides nanoparticle conjugated synthetic opioid prodrugs with long-lived bioavailability, that do not compromise systemic analgesic effects and do not induce opioid withdrawal symptoms. Applications include the prevention and/or treatment of opioid-induced constipation (OIC).

Background

Opioids are the mainstay for cancer and non-cancer pain management. However, their use is associated with multiple adverse effects with the most common and distressing being constipation. The high prevalence of opioid-induced constipation (IC) among different populations and rare tolerance development to constipation significantly limit opioid usage.

The traditional treatment of OIC by employing laxatives provides unsatisfactory clinical results. Several other pharmacological interventions have been applied to address OIC, including "opioid switch" (such as switching from morphine to transdermal fentanyl, transdermal buprenorphine, methadone, or tapentadol, 5-HT4 agonists (such as prucalopride), and type-2 chloride channel activators (such as lubiprostone). However, none of these interventions provides a predictable, straightforward and satisfactory solution to the problem.

The pathophysiology of OIC is attributed primarily to the activation, by the opioid that is administered, of peripheral mu opioid receptor (MOR) in the gastrointestinal (GI) tract. Most of the aforementioned therapies have only limited effectiveness for OIC because they do not directly address this underlying pathophysiology of OIC.

Several agents have been developed that are relatively mu- and kappa-selective opioid antagonists, e.g. Naloxone. However, this agent has a low oral bioavailability (~2%) due to extensive hepatic first-pass metabolism. Its role in OIC has been extensively studied for over a decade, yet reversal of desired analgesia and/or precipitation of withdrawal symptoms are frequently seen with only modestly improved laxation after immediate release of naloxone. A fixed dose combination of extended-release naloxone and oxycodone overcame these drawbacks and significantly improved bowel function due to its improved pharmacokinetic property. On the other hand, this fixed-dose combination is not applicable to many patients e.g. those with chronic liver diseases or those using other opioid analgesics.

The selective MOR antagonist, 17-cyclopropylmethyl-3, 14 β-dihydroxy-4,5 α-epoxy-6 β-[(4-pyridyl)acetamido] morphinan (NAP) also acts as a periphery-selective MOR ligand. NAP displays high binding affinity for the mu opioid receptor (MOR) with more than 700-fold selectivity over the delta opioid receptor (DOR) and more than 150-fold selectivity over the kappa opioid receptor (KOR), and has been shown to increase intestinal motility in morphine-pelleted mice (see U.S. Pat. No. 8,980,908, the complete contents of which is herein incorporated by reference in entirety). Thus, NAP is a promising compound to address the peripheral side effects of opioids. However, this agent also suffers from limited bioavailability.

There is a need in the art for compositions and methods to safely and effectively deliver periphery-selective MOR antagonists in a manner that provides long-lived bioavailability without compromising systemic analgesic effects and without inducing opioid withdrawal symptoms when their use is discontinued.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Provided herein are nanoparticle conjugated synthetic opioid prodrugs with long-lived bioavailability. The prodrugs target the peripheral mu opioid receptor (MOR) and thus do not compromise the analgesic effects of opioids administered for pain relief, which tend to target opioid receptors in the brain, and do not induce opioid withdrawal symptoms, when their use is discontinued. Certain of the prodrugs are especially useful for the prevention and/or treatment of unwanted opioid-induced side effects such as opioid-induced constipation (OIC). In some cases, the prodrugs are used for pain relief. Due to the long bioavailability, the prodrugs are administered in lesser quantities and/or less frequently than non-prodrug synthetic opioids.

It is an object of this invention to provide compounds having the general Formula I:

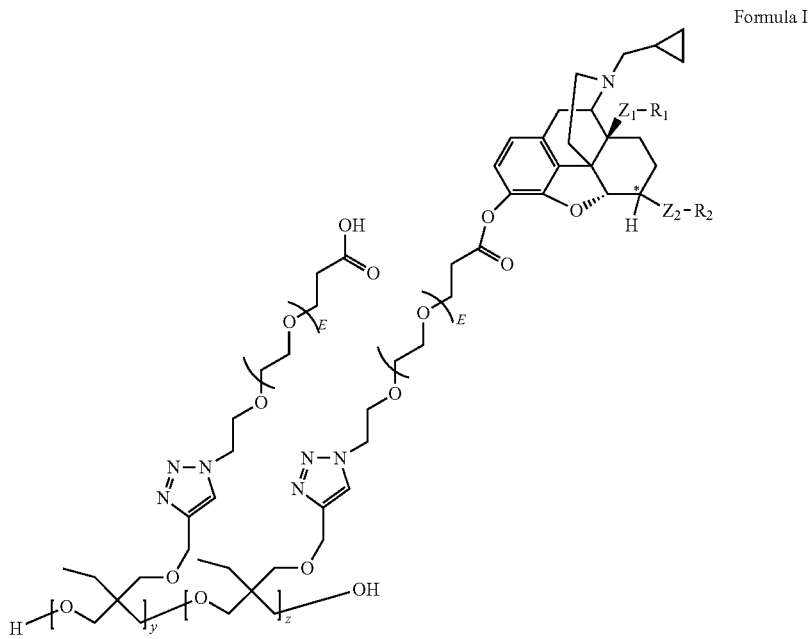

Formula I where
m=0-16;
y=5-20;
z=10-30;
* indicates a chiral center where a configuration is either R or S;

Z1 and Z2 are spacer elements each of which may be present or absent and, if both are present, may be the same or different, and are selected from: an aliphatic moiety; NH; CO; (NHCO)n where n=1-5; (CONH)n where n=1-5; (NHCO)(CH$_2$)n(NHCO), where n=1-5; (NHCO)(CH)n where n=1-5; (CH$_2$)n(NHCO), where n=1-5; and 0; and R1 and R2 may be the same or different and are hydrogen; a substituted or unsubstituted aliphatic moiety or a stereoisomer thereof; or a substituted or unsubstituted aromatic moiety or a stereoisomer thereof;

with the caveat that at least one of R1 and R2 is a substituted or unsubstituted aromatic moiety selected from the group consisting of:

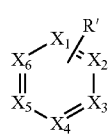

Formula II wherein $X_1$-$X_6$ are independently C, O, N, S or an aliphatic moiety in any combination, and R' is present or absent and if present is hydrogen or a substituted or unsubstituted aromatic or aliphatic moiety; and wherein a bond joining the substituted or unsubstituted aromatic moiety of Formula II to Z1 and/or Z2 is at any of positions $X_1$-$X_6$;

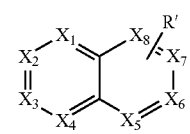

Formula III where $X_1$-$X_8$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula III to Z1 and/or Z2 is located at any of positions $X_1$-$X_8$;

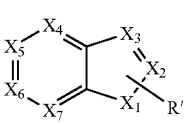

Formula IV where $X_1$-$X_7$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula IV to Z1 and/or Z2 is located at any of positions $X_1$-$X_7$;

5

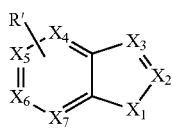
Formula V

6

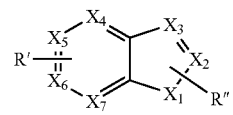
Formula VI where $X_1$-$X_7$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula V to Z1 and/or Z2 is located at any of positions $X_1$-$X_7$; and where $X_1$-$X_7$ are independently C, O, N, S or an aliphatic moiety in any combination and R' and R" are independently the same or different, and are independently present or absent and if present are independently hydrogen or a substituted or unsubstituted aromatic or aliphatic moiety, and wherein a bond joining the substituted or unsubstituted aromatic moiety of Formula VI to Z1 and/or Z2 is located at any of positions $X_1$-$X_7$.

In some aspects, the opioid prodrug is

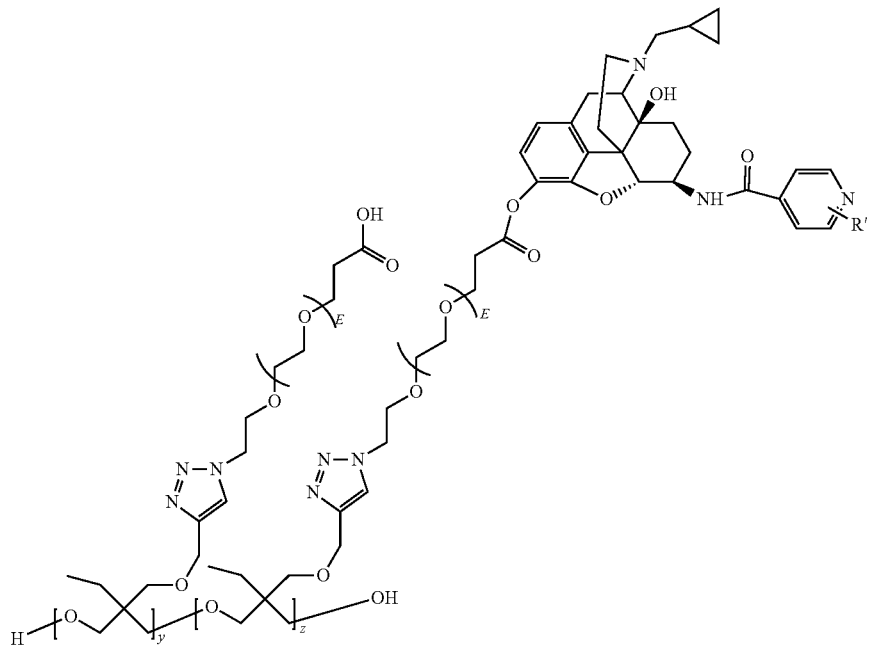

where R' is hydrogen or a substituted or unsubstituted aromatic or aliphatic moiety.

In other aspects, the opioid prodrug is
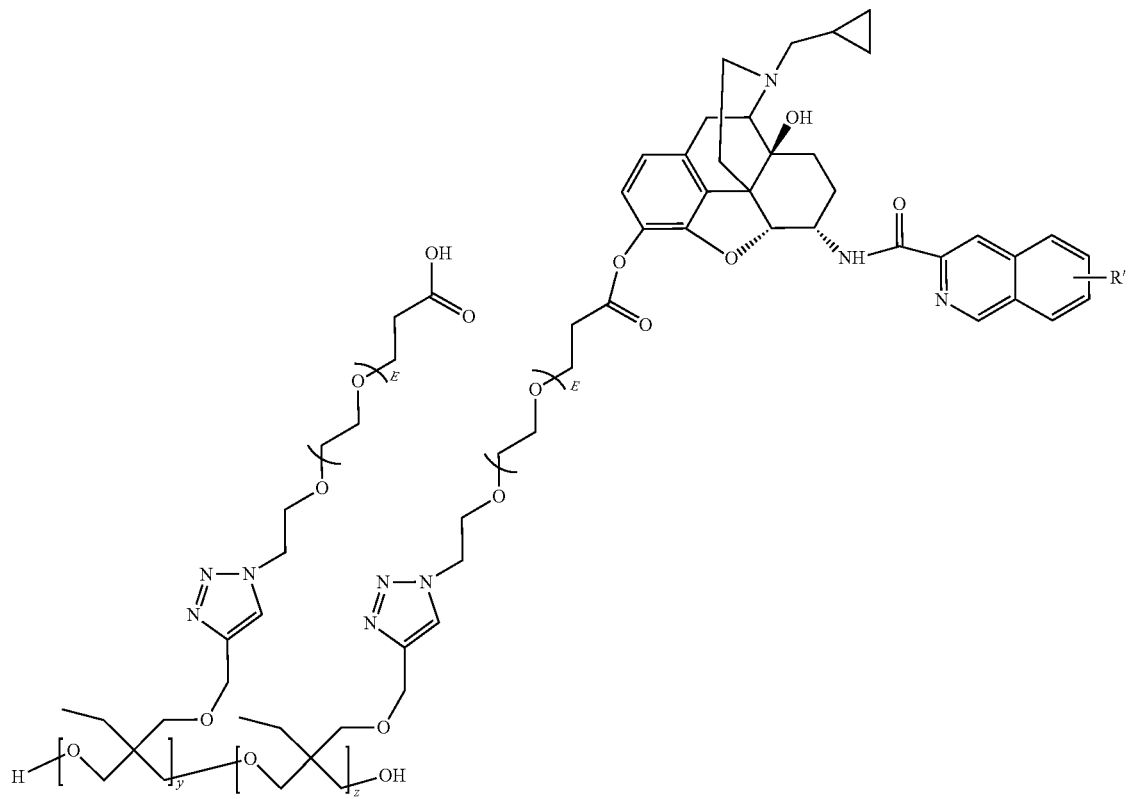
where R' is hydrogen or a substituted or unsubstituted aromatic or aliphatic moiety.
In yet other aspects, the opioid prodrug is
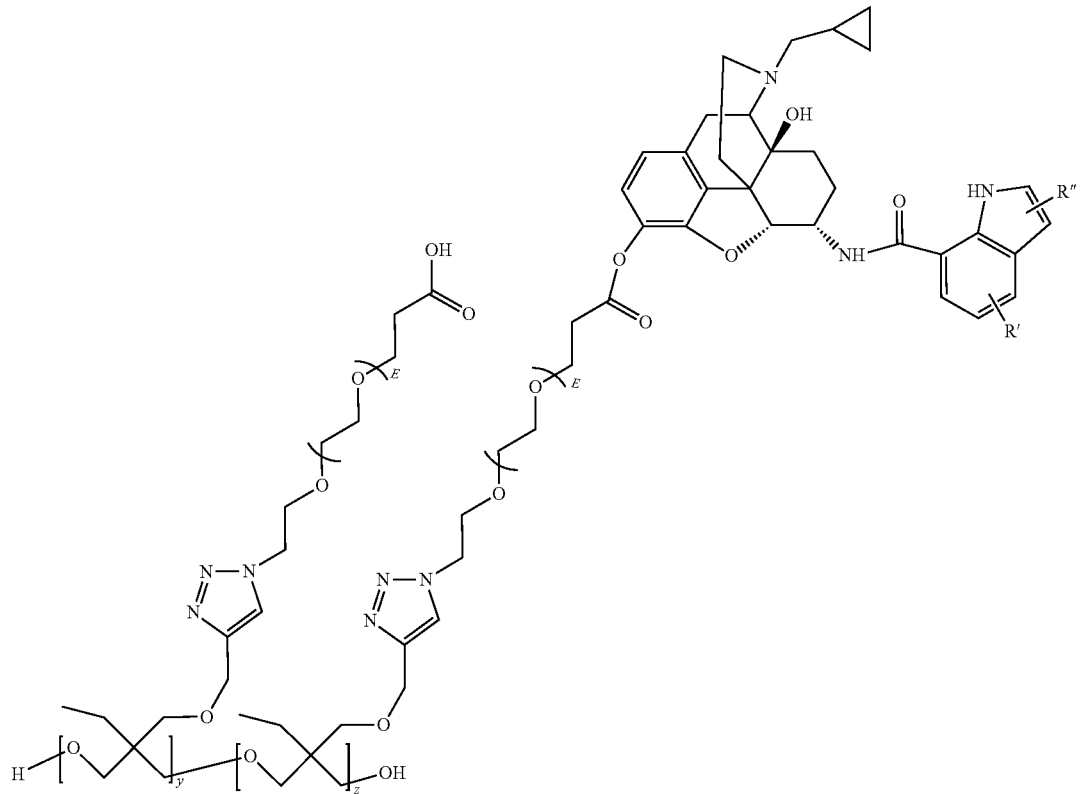

where R' and R" are independently hydrogen or a substituted or unsubstituted aromatic or aliphatic moiety, and are independently present or absent.
In yet other aspects, the opioid prodrug is
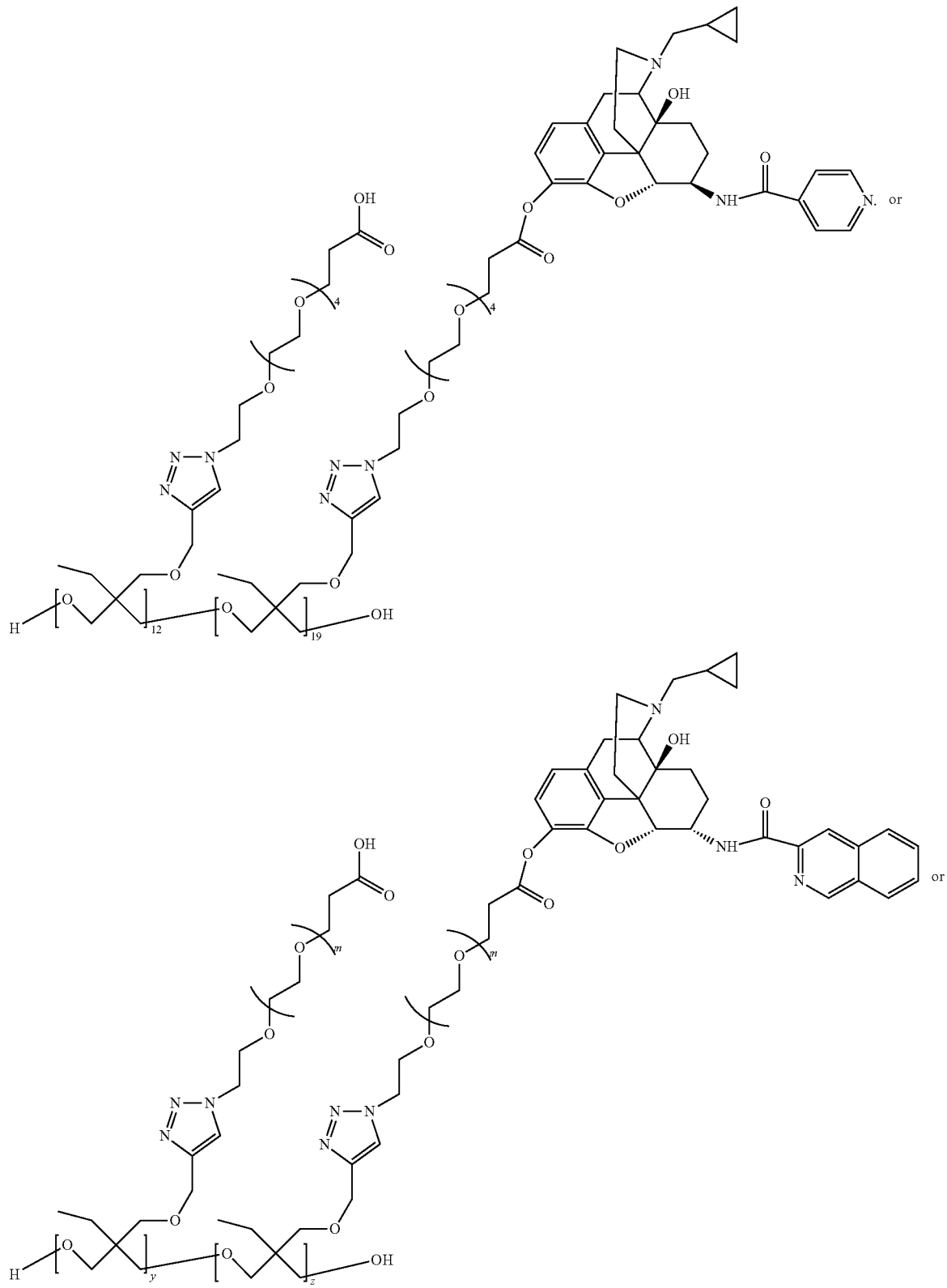

-continued
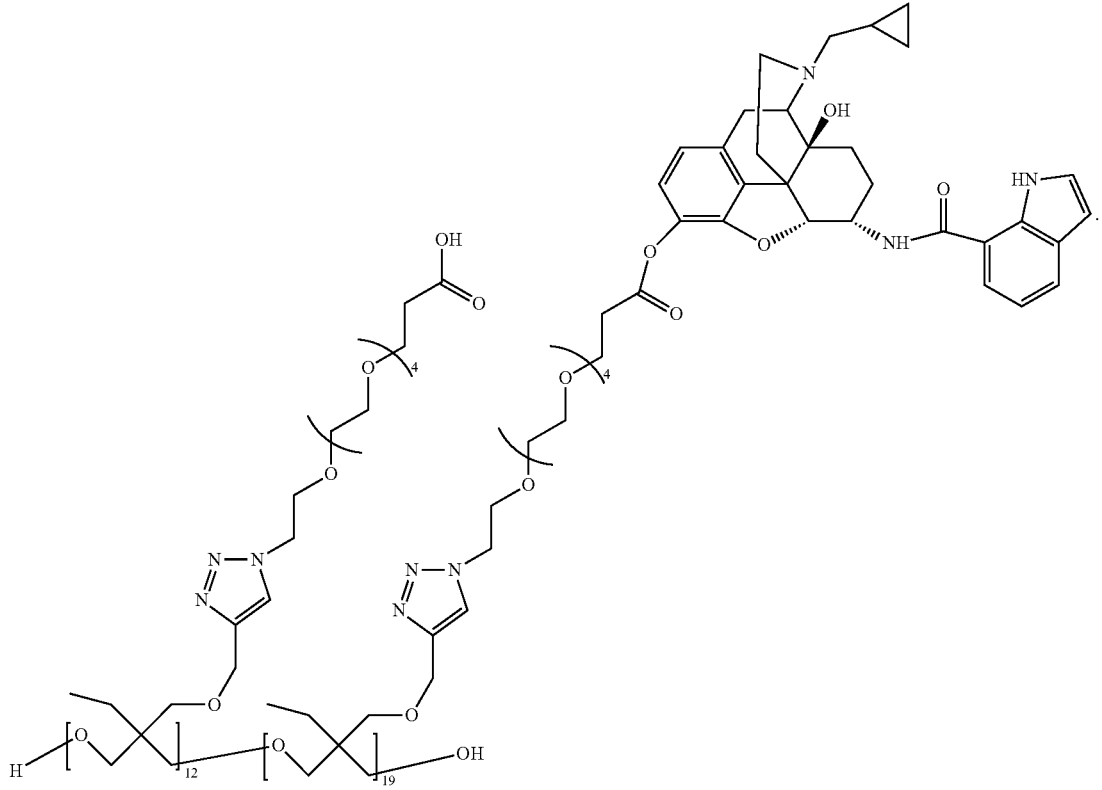
Further provided are methods of preventing or treating opioid induced constipation (OIC) in a subject in need thereof, comprising administering to the subject a therapeutically effective amount of the compound having the general Formula I and particularly the compound
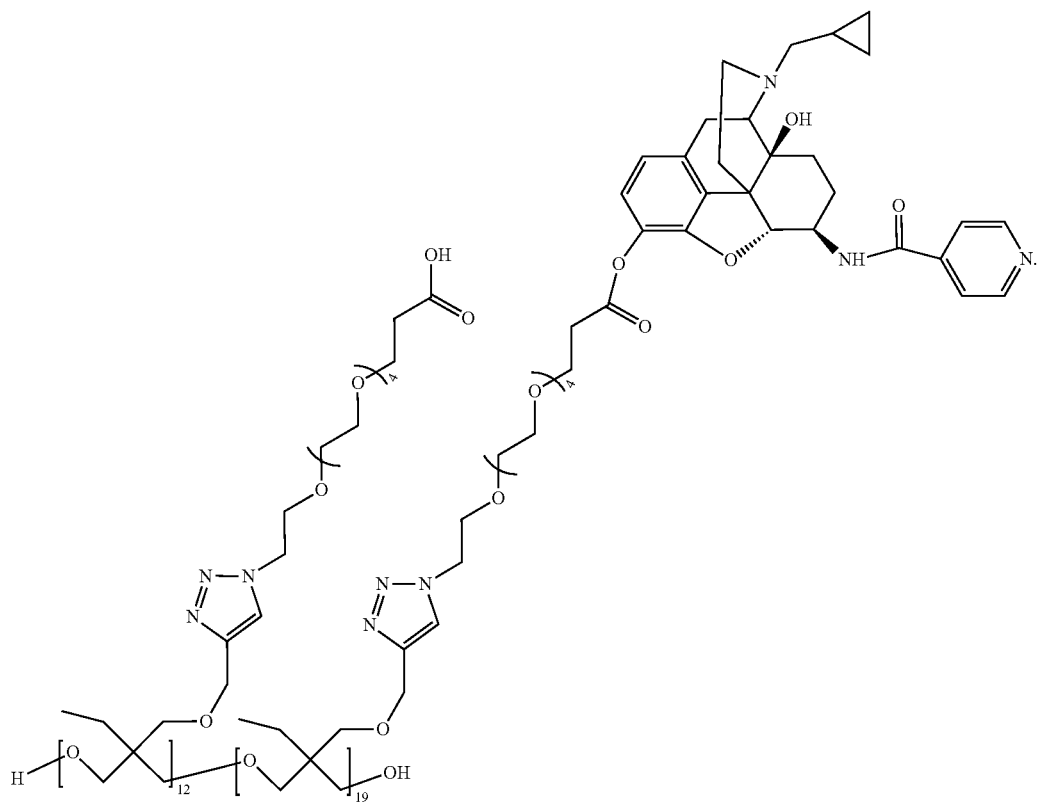

Also provided are methods of treating pain in a subject in need thereof, comprising administering to the subject a therapeutically effective amount of a compound having the general Formula I:

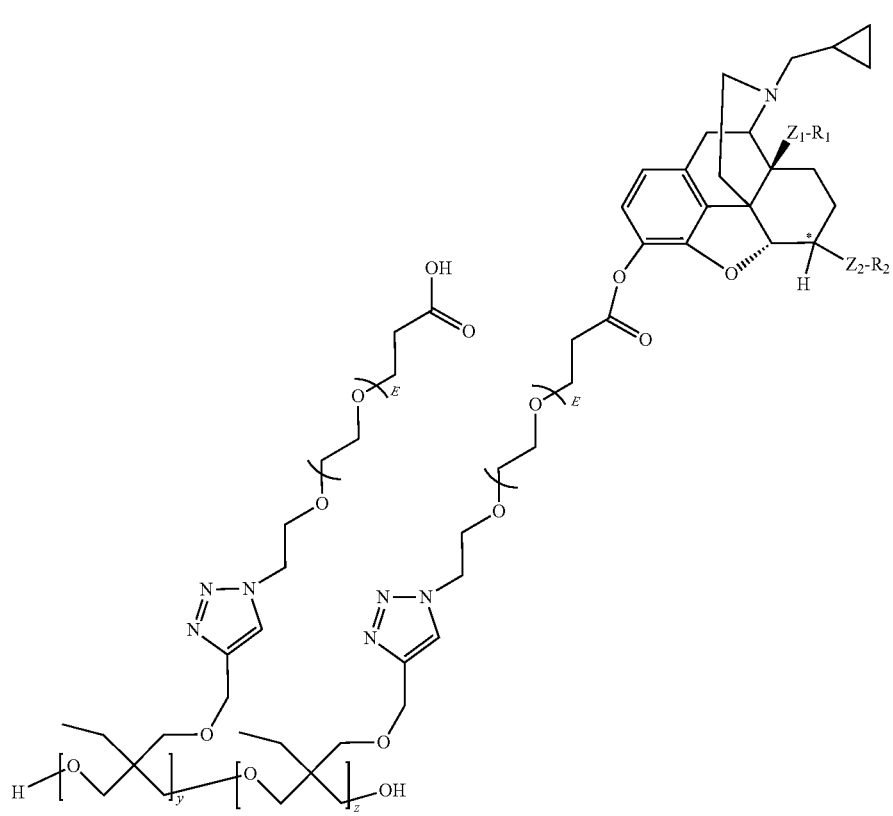

Formula I where
m=0-16;
y=5-20;
z=10-30;
* indicates a chiral center where a configuration is either R or S;
Z1 and Z2 are spacer elements each of which may be present or absent and, if both are present, may be the same or different, and are selected from: an aliphatic moiety; NH; CO; (NHCO)n where n=1-5; (CONH)n where n=1-5; (NHCO)(CH$_2$)n(NHCO), where n=1-5; (NHCO)(CH)n where n=1-5; (CH$_2$)n(NHCO), where n=1-5; and 0; and
R1 and R2 may be the same or different and are
hydrogen; a substituted or unsubstituted aliphatic moiety or a stereoisomer thereof; or a substituted or unsubstituted aromatic moiety or a stereoisomer thereof;
with the caveat that at least one of R1 and R2 is a substituted or unsubstituted aromatic moiety selected from the group consisting of:

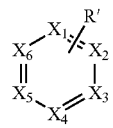

Formula II wherein $X_1$-$X_6$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula II to Z1 and/or Z2 is at any of positions $X_1$-$X_6$;

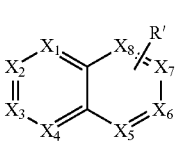

Formula III where $X_1$-$X_8$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula III to Z1 and/or Z2 is located at any of positions $X_1$-$X_8$;

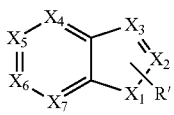

Formula IV where $X_1$-$X_7$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula IV to Z1 and/or Z2 is located at any of positions $X_1$-$X_7$;

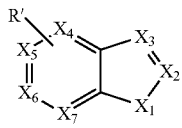

Formula V where $X_1$-$X_7$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula V to Z1 and/or Z2 is located at any of positions $X_1$-$X_7$; and

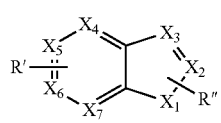

Formula VI where $X_1$-$X_7$ are independently C, O, N, S or an aliphatic moiety in any combination and R' and R" are independently present or absent, and if present are independently hydrogen or a substituted or unsubstituted aromatic or aliphatic moiety, and wherein a bond joining the substituted or unsubstituted aromatic moiety of Formula VI to Z1 and/or Z2 is located at any of positions $X_1$-$X_7$, with the caveat that in some applications, the compound is not

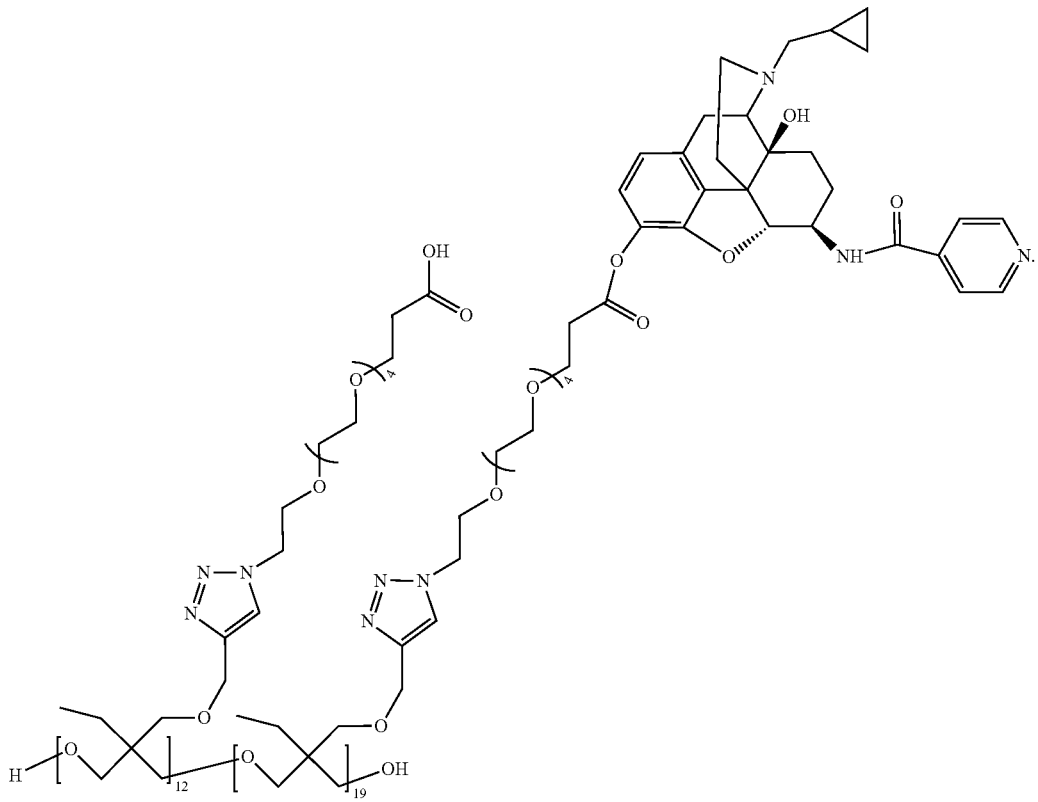

In addition, the invention provides methods of treating a disease or condition selected from the group consisting of: substance addiction, Parkinson's disease, obesity, epilepsy, inflammation, a gastrointestinal tract disorder, AIDs and a psychological brain disorder, comprising administering to the subject a therapeutically effective amount of a compound having the general Formula I:

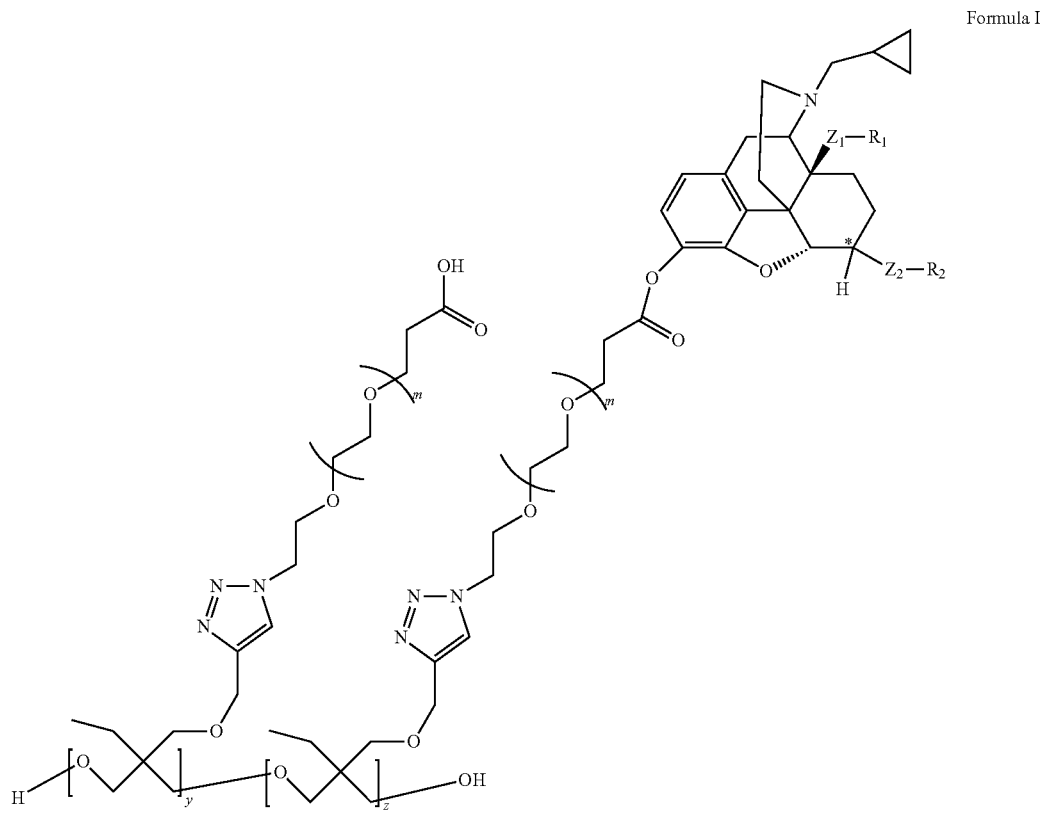

Formula I where m=0-16;

y=5-20;

z=10-30;

* indicates a chiral center where a configuration is either R or S;

$Z_1$ and $Z_2$ are spacer elements each of which may be present or absent and, if both are present, may be the same or different, and are selected from: an aliphatic moiety; NH; CO; (NHCO)n where n=1-5; (CONH)n where n=1-5; (NHCO)(CH)n(NHCO), where n=1-5; (NHCO)(CH)n where n=1-5; (CH$_2$)n(NHCO), where n=1-5; and 0; and $R_1$ and $R_2$ may be the same or different and are hydrogen; a substituted or unsubstituted aliphatic moiety or a stereoisomer thereof; or a substituted or unsubstituted aromatic moiety or a stereoisomer thereof;

with the caveat that at least one of $R_1$ and $R_2$ is a substituted or unsubstituted aromatic moiety selected from the group consisting of:

Formula II wherein $X_1$-$X_6$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula II to Z1 and/or Z2 is at any of positions $X_1$-$X_6$;

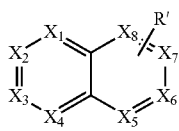

Formula III where $X_1$-$X_8$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula III to Z1 and/or Z2 is located at any of positions $X_1$-$X_8$;

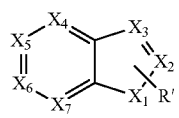

Formula IV where $X_1$-$X_7$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula IV to Z1 and/or Z2 is located at any of positions $X_1$-$X_7$;

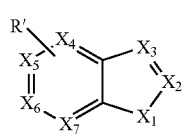

Formula V where $X_1$-$X_7$ are independently C, O, N, S or an aliphatic moiety in any combination and R' is present or absent and if present is hydrogen or a substituted or unsubstituted aromatic or aliphatic moiety, and wherein a bond joining the substituted or unsubstituted aromatic moiety of Formula V to Z1 and/or Z2 is located at any of positions $X_1$-$X_7$; and

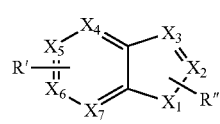

Formula VI where $X_1$-$X_7$ are independently C, O, N, S or an aliphatic moiety in any combination and R' and R" are independently present or absent, and if present are independently hydrogen or a substituted or unsubstituted aromatic or aliphatic moiety, and wherein a bond joining the substituted or unsubstituted aromatic moiety of Formula VI to Z1 and/or Z2 is located at any of positions $X_1$-$X_7$.

In some aspects, the substance addiction is selected from the group consisting of: opioid addiction, cocaine addiction, alcohol addiction, amphetamine addiction, methamphetamine addiction and bath salt addiction. In other aspects, the opioid addiction is heroin addiction, morphine addiction, oxycodone addiction or methadone addiction. In yet further aspects, the psychological brain disorder is selected from the group consisting of such as depression, schizophrenia, bipolar disorder, schizoaffective disorder and gambling addiction.

The invention also provides methods of producing an opioid prodrug, comprising i) reacting a free-base form of an opioid with polyethylene glycol (PEG) azide under conditions suitable to form an opioid-PEG-azide conjugate; ii) performing ring-opening polymerization of acetylene-functionalized 3-ethyl-3-(hydroxymethyl)oxetane (EAMO) monomers under conditions suitable to generate back bones of polymerized EAMO [P(EAMO)]; and iii) reacting the P(EAMO) with the opioid-PEG-azide conjugate via a click reaction under conditions suitable to form a P(EAMO)-opioid-PEG conjugate. In some aspects, the opioid that is synthesized is 17-cycopropylmethyl-3,14β-dihydroxy-4,5 α-epoxy-6β-[(4-pyridyl)acetamido]morphinan (NAP).

DETAILED DESCRIPTION

Figure 1:
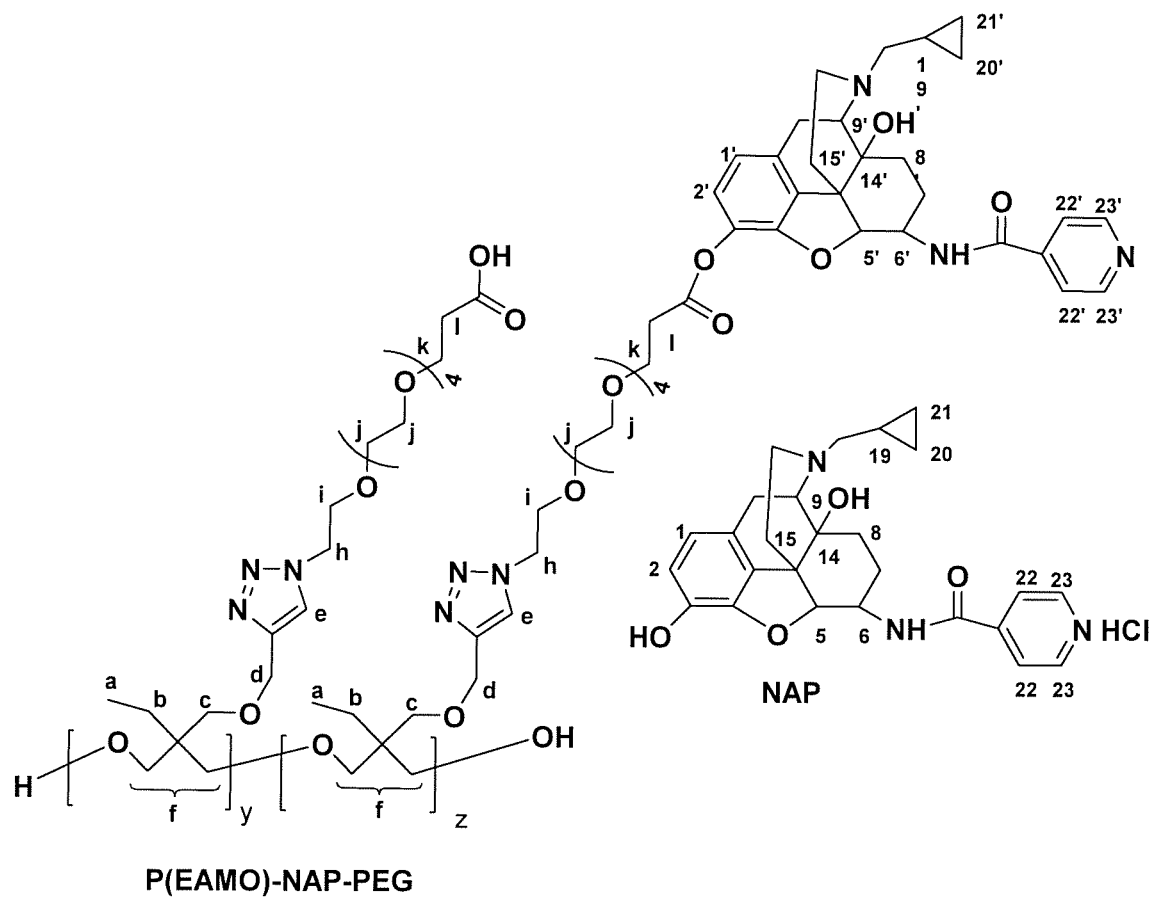
FIG. 1. NAP and nanoconjugated NAP (P(EAMO)-NAP-PEG).

Provided herein are nanoparticle conjugated synthetic opioid prodrugs that target the peripheral MOR. The prodrugs have the general formula:

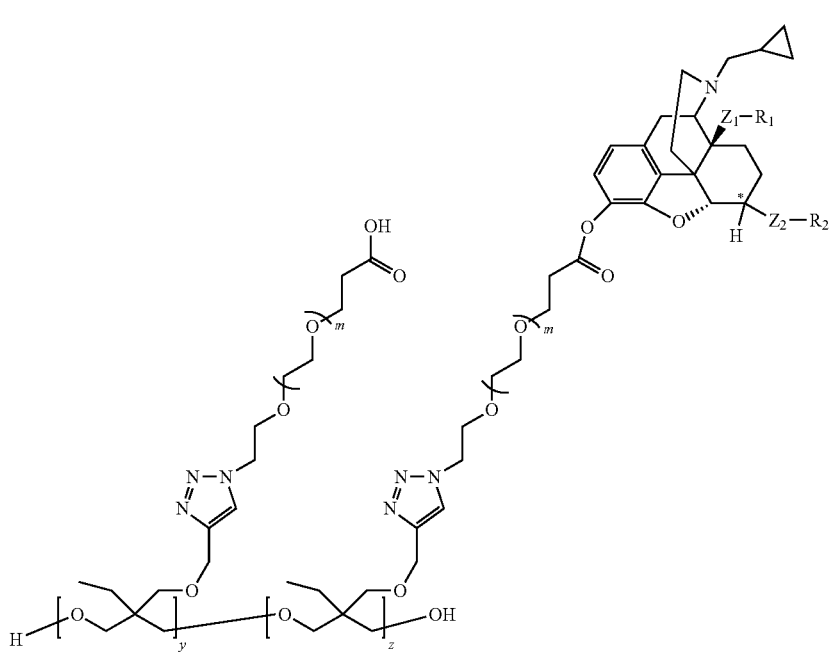

Formula I where
m=0-16;
y=5-20;
z=10-30;
* indicates a chiral center where a configuration is either R or S;

Z1 and Z2 are spacer elements each of which may be present or absent and, if both are present, may be the same or different, and are selected from: an aliphatic moiety; NH; CO; (NHCO)n where n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and 0; and R1 and R2 may be the same or different and are hydrogen, a substituted or unsubstituted aliphatic moiety or a stereoisomer thereof, or a substituted or unsubstituted aromatic moiety, or a stereoisomer thereof; with the caveat that at least one of R1 and R2 is a substituted or unsubstituted aromatic moiety selected from the group consisting of:

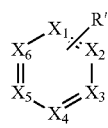

Formula II wherein $X_1$-$X_6$ are independently C, O, N, or S in any combination, and a bond joining the substituted or unsubstituted aromatic moiety of Formula II to Z1 and/or Z2 is at any of positions $X_1$-$X_6$; and wherein R' is present or absent and if present is hydrogen or a substituted or unsubstituted aromatic or aliphatic moiety;

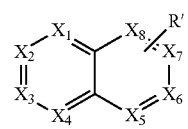

Formula III wherein $X_1$-$X_8$ are independently C, O, N, or S in any combination, and a bond joining the substituted or unsubstituted aromatic moiety of Formula III to Z1 and/or Z2 is located at any of positions $X_1$-$X_8$; and wherein R' is present or absent and if present is hydrogen or a substituted or unsubstituted aromatic or aliphatic moiety; and

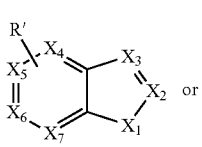

Formula IV

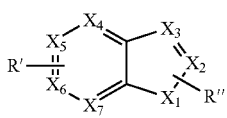

Formula V

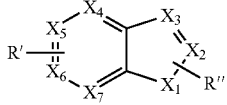

Formula VI where X1-X7 are independently C, O, N, S in any combination, and a bond joining the substituted or unsubstituted aromatic moiety of Formula IV, Formula V or Formula VI to Z1 and/or Z2 is located at any of positions $X_1$-$X_7$; and wherein, for Formulas IV and V, R may be present or absent and if present is hydrogen or a substituted or unsubstituted aromatic or aliphatic moiety; and for Formula VI, R' and R" are independently present or absent and if present may independently be hydrogen or a substituted or unsubstituted aromatic or aliphatic moiety.

Exemplary equivalents of

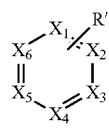

include but are not limited to:

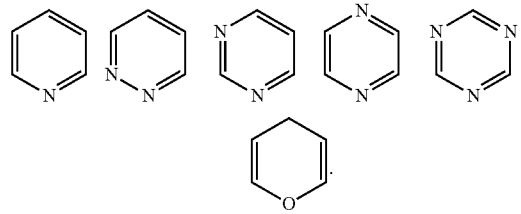

Exemplary equivalents of

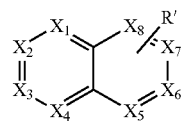

include but are not limited to:

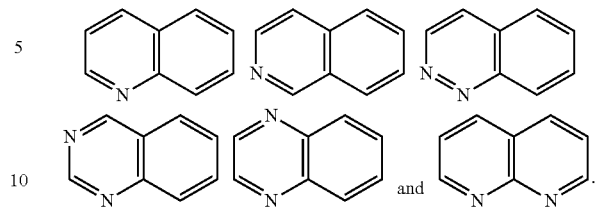

Exemplary equivalents of

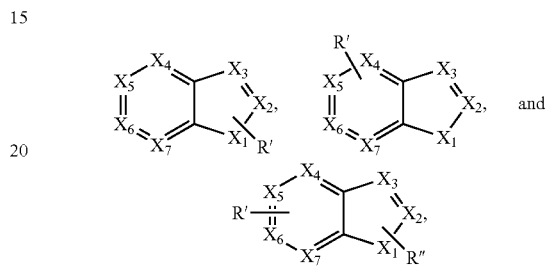

include but are not limited to:

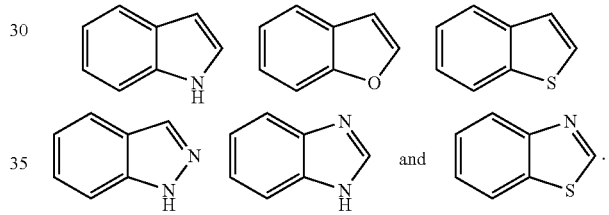

In some aspects, the compound is

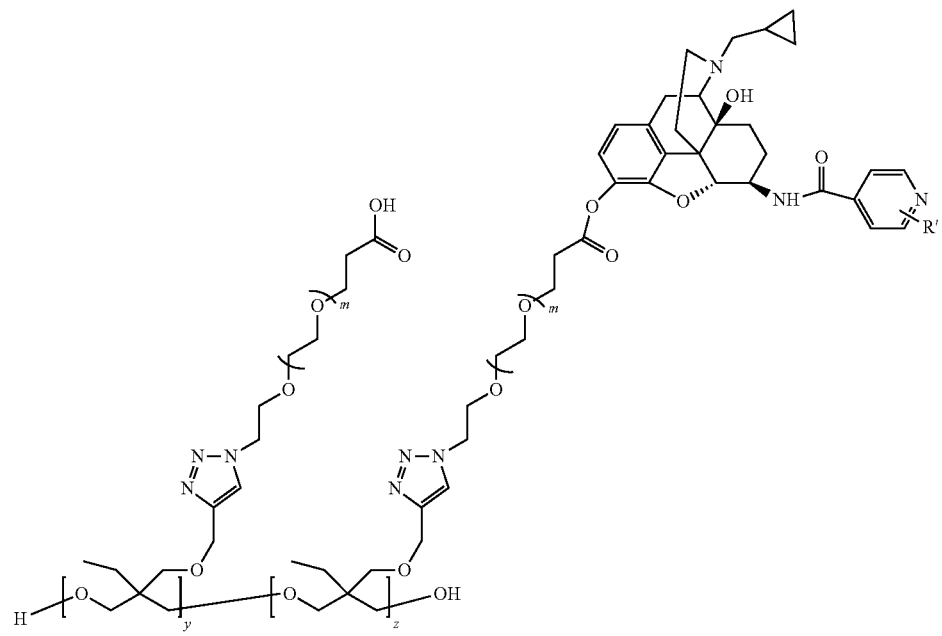

where
m=0-16; y=5-20; z=10-30; and
R' is present or absent and if present is hydrogen or a substituted or unsubstituted aromatic or aliphatic moiety.
In other aspects, the compound is
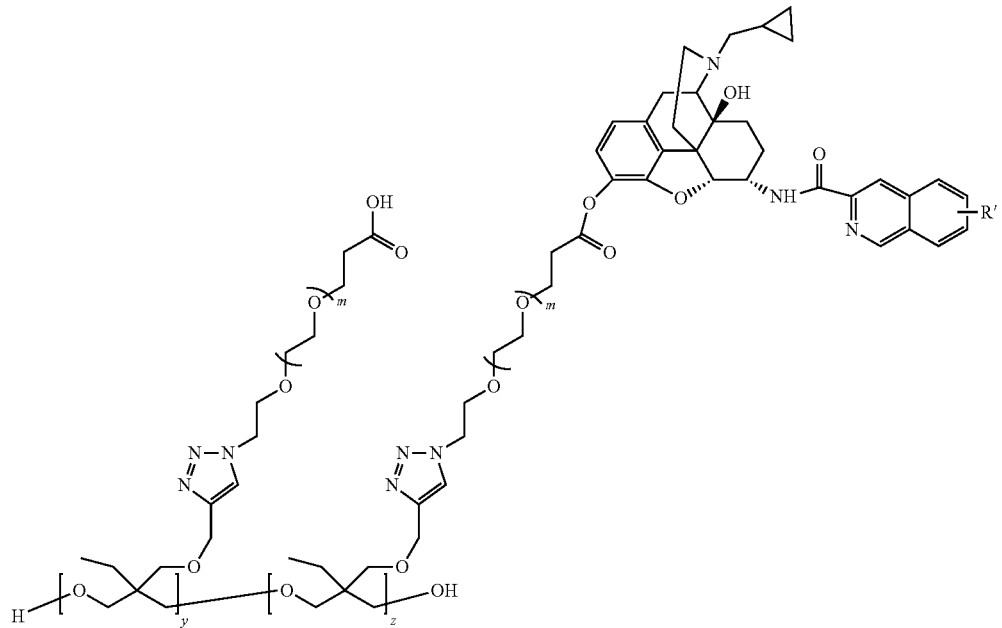
where
m=0-16; y=5-20; z=10-30;
R' is hydrogen or a substituted or unsubstituted aromatic or aliphatic moiety.
In other aspects, the compound is
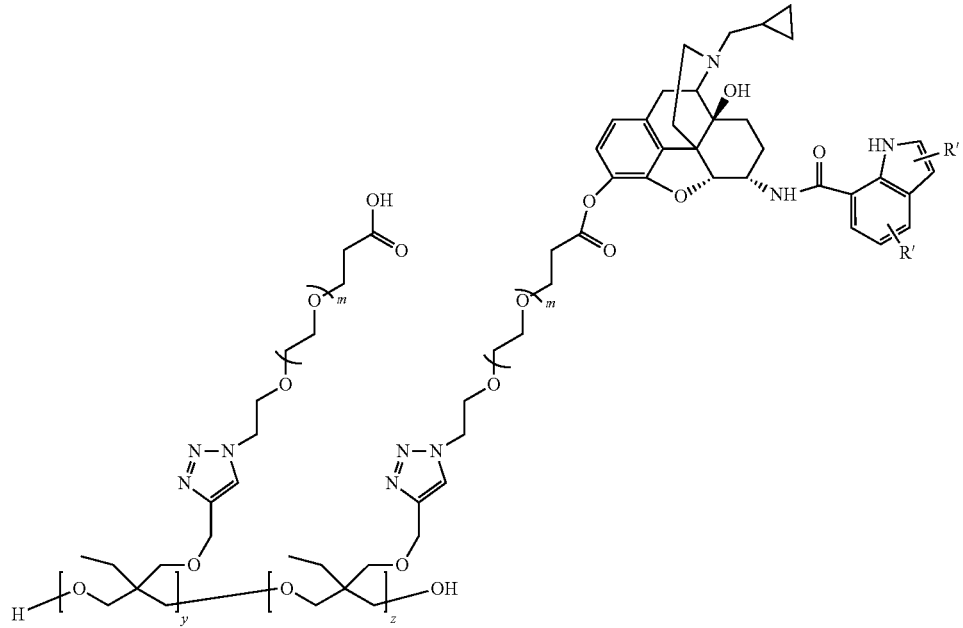

where
m=0-16; y=5-20; z=10-30; and
R' and R" are independently hydrogen or a substituted or unsubstituted aromatic or aliphatic moiety, and may be independently present or absent.
In one aspect, the compound is
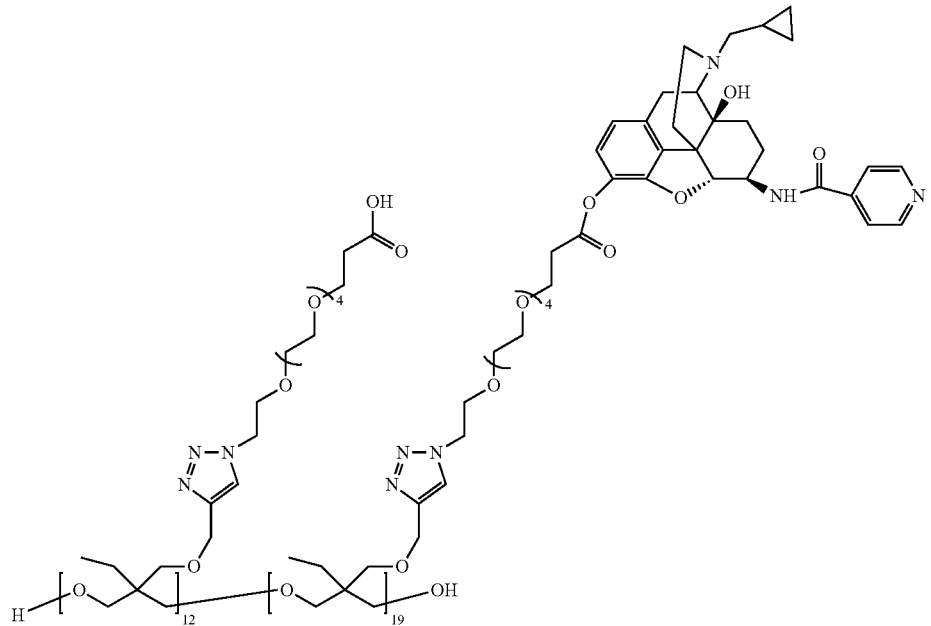
P(EAMO)-NAP-PEG where NAP is 17-cyclopropylmethyl-3,14β-dihydroxy-4,5 α-epoxy-6 β-[(4-pyridyl)acetamido] morphinan.
In another aspect, the compound is
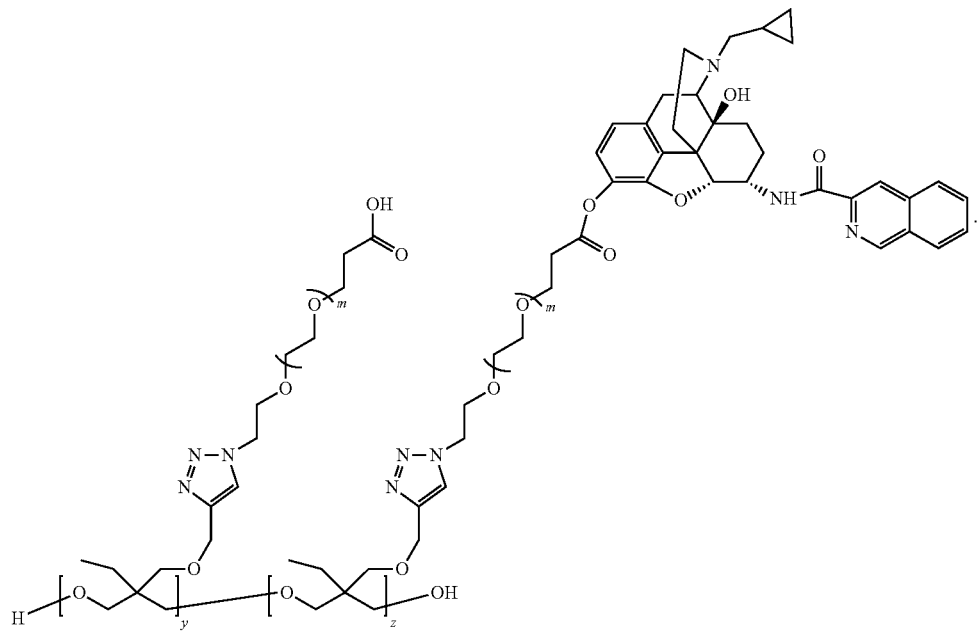

P(EAMO)-NAQ-PEG where "NAQ" refers to 17-cyclopropylmethyl-3,14 β-dihydroxy-4,5 α-epoxy-6 α-(isoquinoline-3'-carboxamido)morphinan.

In another aspect, the compound is

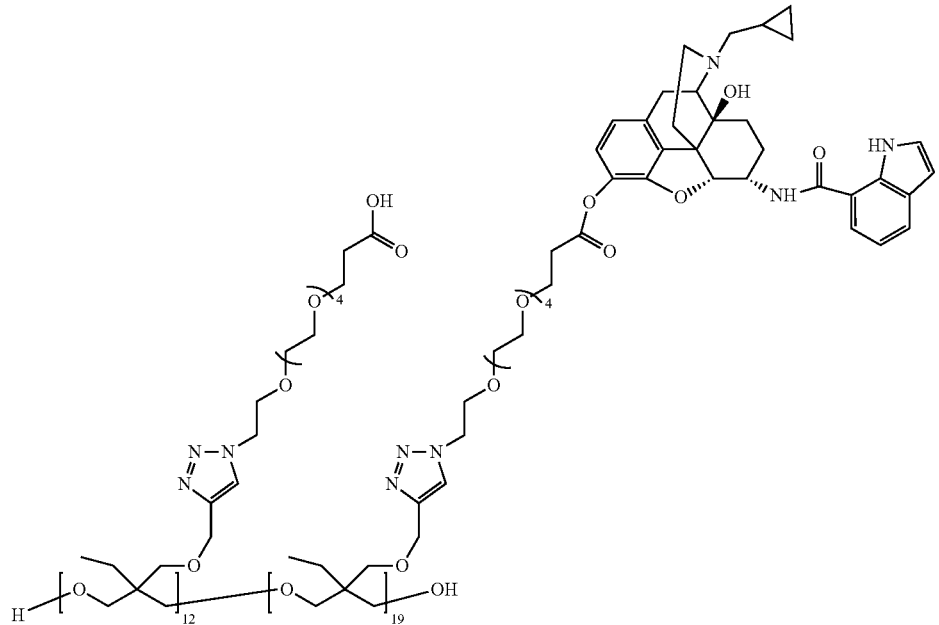

P(EAMO)-NAN-PEG where NAN is 17-cyclopropylmethyl-3,14β-dihydroxy-4,5α-epoxy-6α-(indole-7'-carboxamido)morphinan.

By "is located at any of positions $X_1$-$X_7$ or $X_1$-$X_8$" we mean that a bond may be formed to join the substituted or unsubstituted aromatic moiety of Formulas II-VI to the linkers Z1 and/or Z2 may be formed between the linker and any of the atoms in the substituted or unsubstituted aromatic moiety, as chemically possible.

Further opioids that may be used in the practice of the invention include but are not limited to those described in U.S. Pat. No. 8,980,908, the complete contents of which is incorporated by reference, and the derivatives disclosed therein.

Exemplary aliphatic moieties include but are not limited to various 1-10 alkyls, which may be branched or unbranched, e.g. methyl, ethyl, propyl, butyl, pentyl, etc. and isomers thereof; various carbon moieties which comprise at least one double bond, e.g. 1-10 carbon alkenes which comprise a double bond, and isomers thereof; various 1-10 carbon dienes with comprise 2 double bonds and isomers thereof, etc. Further exemplary alkyls include but are not limited to: various 3-7-membered carbon rings, usually a 5 or 6-membered carbon ring, which may be substituted or unsubstituted, and may be saturated or unsaturated; and phenyl. All of these exemplary aliphatic moieties may be unsubstituted or substituted e.g. with O, H, N, S, etc., when chemically possible.

Prodrugs described herein advantageously target the peripheral MOR receptor. As such, they are selective or specific for the MOR. Generally, these prodrugs have an affinity (as of Ki) for MOR that is in a range of from about 0.1 to 10 nM, i.e. about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 or 10 nM. These MOR selective prodrugs thus do not compete, or do not significantly compete, with opioids that bind to central nervous system receptors, and do not diminish the effects thereof. However, they do interfere with the binding of other opioids to MOR. The lack or decrease of binding to MOR by other opioids prevents or reduces the changes in gut motility that otherwise results from their binding to MOR, and prevents or treats (relieves, lessens, etc.) constipation that would otherwise occur. Others of the prodrugs described herein do exhibit some residual ability to bind to CNS opioid receptors, and as such, they may be used to treat or prevent e.g. pain, symptoms of withdrawal from opioids, and other similar conditions. These compounds are advantageously used for these purposes because their effects are milder than those of opioids (such as morphine or heroin) and thus they are less apt to cause addiction with extended use, and/or less likely to cause symptoms of withdrawal when their use is discontinued.

The compounds described herein are generally delivered (administered) in a pharmaceutical composition, and the invention also provides compositions and formulations comprising the compounds described herein, and/or pharmaceutically acceptable salts thereof. The preparation of such compositions is known to those of skill in the art. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts.

If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99% (e.g., 5% or 10% to 20%, 30%, 40%, 50%, or 60% of one or more compounds with the remainder being pharmaceutical carriers, excipients and/or other ingredients). Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compounds described herein may be administered alone, as a single active agent, or in combination with one or more other active agents. "In combination" refers to both sequential administration (e.g. one agent is administered after the other), and administration of a mixture of both active agents. Exemplary combinations include but are not limited to combinations of a compound of the invention, e.g. (P(EAMO)-NAP-PEG), with morphine, oxycodone, methadone, etc. In some aspects, the combinations are fixed dose combinations.

The recipient of the compound is usually a mammal, and may be a human, although veterinary applications are also encompassed. The amount that is administered varies based on several factors, as will be understood by those of skill in the art. For example, the dose and frequency of administration varies according to the type of condition or disease for which the opioid is administered, the severity of the opioid side effects, the opioid that is administered, gender, age, weight, general physical condition, genetic background, etc. of the individual, as well as whether or not the individual has other diseases or conditions that might impinge on the treatment. Generally, the dose will be in the range of from about 0.01 to about 1000 mg/kg of body weight (e.g., about 0.1, 0.5, 1.0, 10, 20, 30, 40, 50, 60, 70, 80, 90, 100, 125, 150, 175, 200, 225, 250, 275, 300, 325, 350, 375, 400, 425, 450, 475 or 500 mg/kg, etc.).

The compounds are administered by any suitable route including but not limited to: inoculation or injection (e.g. intravenous, intraperitoneal, intramuscular, subcutaneous, intra-aural, intraarticular, intramammary, and the like), by topical application and/or by absorption through epithelial or mucocutaneous linings (e.g., nasal, oral, vaginal, rectal, gastrointestinal mucosa, and the like); or by inhalation (e.g. as a mist or spray). Typically, the mode of administration is oral or by injection. In addition, the compositions may be administered in conjunction with other treatment modalities such as other medicaments (e.g. other pain medications, other agents that counteract unwanted opioid-induced side effects), chemotherapeutic agents, other types of therapy (e.g. exercise, surgery, psychotherapy, etc.), and the like.

Conditions and symptoms that are prevented and/or treated using the compounds described herein include but are not limited to: pain of any type, including neuropathic pain, with the caveat that the compound P(EAMO)-NAP-PEG is not used for the treatment of pain; substance abuse and addiction (e.g. opioid, cocaine, alcohol, amphetamine, methamphetamine, bath salts, etc.) in which case the present non-addictive compounds can be substituted for the addictive substance; Parkinson's disease; obesity; epilepsy; inflammation; gastrointestinal tract disorders such as constipation and irritable bowel syndrome (IBS); AIDs; various psychological disorders such as depression, schizophrenia, bipolar disorder, schizoaffective disorder, gambling addiction, etc.; and others. The addictions (dependencies) that may be treated include both recreational addictions which occur as the result of illegal substance abuse, and addictions that result from the legal administration of drugs under the care of a medical professional, e.g. to treat pain. For example, prodrugs based on NAQ are especially useful for the treatment of addiction.

The compound P(EAMO)-NAP-PEG (depicted above) is especially suitable for use in the prevention and/or treatment of opioid induced constipation (OIC). For example, if P(EAMO)-NAP-PEG is used prior to or at an early stage (e.g. at the beginning) of administration of an opioid (such as morphine, oxycodone, methadone, etc.), OIC can be prevented. In such aspects, the opioid and the prodrug may be administered separately (e.g. sequentially), or may be administered as a mixture in a single composition. Alternatively, P(EAMO)-NAP-PEG can be administered at any time after administration of a constipation-inducing opioid has begun, e.g. to treat OIC that is developing or that has already developed in the patient. Accordingly, OIC can be prevented, treated or lessened, i.e. the degree or frequency of OIC may be lessened.

Those of skill in the art will recognize that "prevention" and "treatment", to be beneficial, need not completely eliminate all unwanted symptoms of, e.g. pain, OIC, etc. Much benefit can accrue from the lessening of symptoms to a more manageable or tolerable level, or to a level at which other agents can be used to provide further relief.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Example 1. Synthesis and Testing of an Exemplary Synthetic Opioid Prodrug

Water-soluble cytocompatible PEG-grafted polyoxetane brush polymers can be synthesized by 1) ring-opening polymerization of acetylene-functionalized 3-ethyl-3-(hydroxymethyl)oxetane (EAMO) monomers to generate a back bone of polymerized EAMO [P(EAMO)]; followed by 2) a click reaction with methoxypolyethylene glycol azide (mPEG-azide). The uniformly distributed alkyne pendant groups on the resulting molecule, P(EAMO)-PEG, make this platform well suited for delivery of therapeutic agents such as 17-cyclopropylmethyl-3,14β-dihydroxy-4,5α-epoxy-6β-[(4-pyridyl)acetamido]morphinan (NAP). However, possible challenges and limitations of nanoconjugated NAP include potential difficulty in controlling and optimizing the surface coverage density and retention of an active conformation.

The present Example describes investigations into the possible use of the P(EAMO)-PEG carrier for NAP delivery to the gastrointestinal tract. As described herein, NAP was successfully linked to P(EAMO) via a PEG spacer via one end click coupling to the P(EAMO) polymer through triazole formation, and with the other end linking NAP through an ester bond (FIG. 1). The resulting NAP nanoparticles were investigated for their therapeutic properties in vitro and in vivo and were found to be effective.

Materials and Methods

Materials

Copper (I) bromide (CuBr), 2,2'-bipyridyl-4-dimethylaminopyridine (DMAP), N-(3-dimethylaminopropyl)-N'-ethylcarbodiimide hydrochloride (EDC), triethylamine (Et$_3$N), magnesium sulfate (MgSO$_4$), deuterated solvents, and routine organic solvents were purchased from Acros (Morris Plains, N.J.). A short heterobifunctional PEG derivative, acid-PEG-azide (MW=335 Da, n=5) was purchased from Biomatrik Inc. (Jiaxing, Zhejiang, China). Dialysis tubing and snakeskin MWCO 3500 were obtained from Thermo Fisher Scientific (Pittsburgh, Pa.).

NAP was synthesized as described (Li, et al. *J Med Chem* 2009, 52, 1416-27).

P(EAMO) was synthesized as described (Zolotarskaya, et al. Macromolecules. 2013, 46, 63-71).

Instrumentation $^1$H NMR spectra were recorded on a Bruker AVANCEIII 600 MHz spectrometer. FTIR spectra were obtained on a Megna-IR 760 spectrometer using KBr pellets. Fluorescence emission spectra were recorded on a fluorescence spectrometer QM4 (Photon Technology International, Birmingham, N.J.). Particle size and zeta potential were measured on Malvern Zetasizer Nano ZS90 apparatus (Malvern Instruments, Worcestershire, U.K.)

Synthesis of P(EAMO)-NAP-PEG Nanoconjugates

The synthesis of P(EAMO)-NAP-PEG Nanoconjugates was performed as illustrated in Scheme 1. Briefly:

Step 1. Coupling of NAP to PEG-azide via a Steglich esterification (Neises and Steglich (1978) Angew. Chem. Int. Ed. 17 (7): 522-524). Briefly, to a suspension of NAP (50 mg) in 5 ml of dichloromethane (DCM) at 0° C. was added dropwise 30 μl of Et$_3$N. The solution was stirred for 30 minutes and subjected to rotary evaporation to remove DCM to obtain crude solid NAP free base (77 mg, 0.17 mmol). PEG-azide (75 mg, 0.22 mmol), and 4-dimethylaminopyridine (DMAP, 20 mg, 0.16 mmol) were dissolved in 5 ml of DCM. Following addition of 1-Ethyl-3-(3-dimethylaminopropyl) carbodiimide (EDC, 75 mg, 0.4 mmol), the reaction mixture was stirred overnight at room temperature and then poured into 10 ml of cold water. Following extraction with DCM (20 ml×3), the combined DCM solution was dried over MgSO$_4$. Crude NAP-PEG-azide product was then obtained by removing DCM under reduced pressure and used without further purification.

Step 2. Coupling of NAP-PEG-azide to P(EAMO). A mixture of P(EAMO) (23 mg, 4.75 μmol, possessing 31 repeat units, i.e., n=31), crude NAP-PEG-azide (100 mg), and 2, 2'-bipyridyl (24 mg, 0.16 mmol) was dissolved in 1.5 ml of dry dimethyl sulfoxide (DMSO) and degassed using the freeze-pump-thaw method. The flask was filled with nitrogen and a DMSO solution of CuBr (11 mg, 77 μmol) was added. After an overnight reaction at room temperature, the reaction solution was poured into 20 ml of cold water and stirred for 1 h. The resulting precipitated solid was filtered, washed with water, and dried. The crude P(EAMO)-NAP-PEG conjugates were dissolved in DCM and centrifuged at 15.6 kg force for 1 h. Following removal of DCM under reduced pressure, the obtained residue was suspended in 10 ml of ether, stirred overnight, filtered, washed with ether three times (4 ml×3), and then vacuum dried. For further purification, the conjugates were washed with ethylenediaminetetraacetic acid (EDTA)/DCM, filtered, and vacuum dried.

Scheme 1. Synthesis of P(EAMO)-PEG-NAP nanoconjugates.

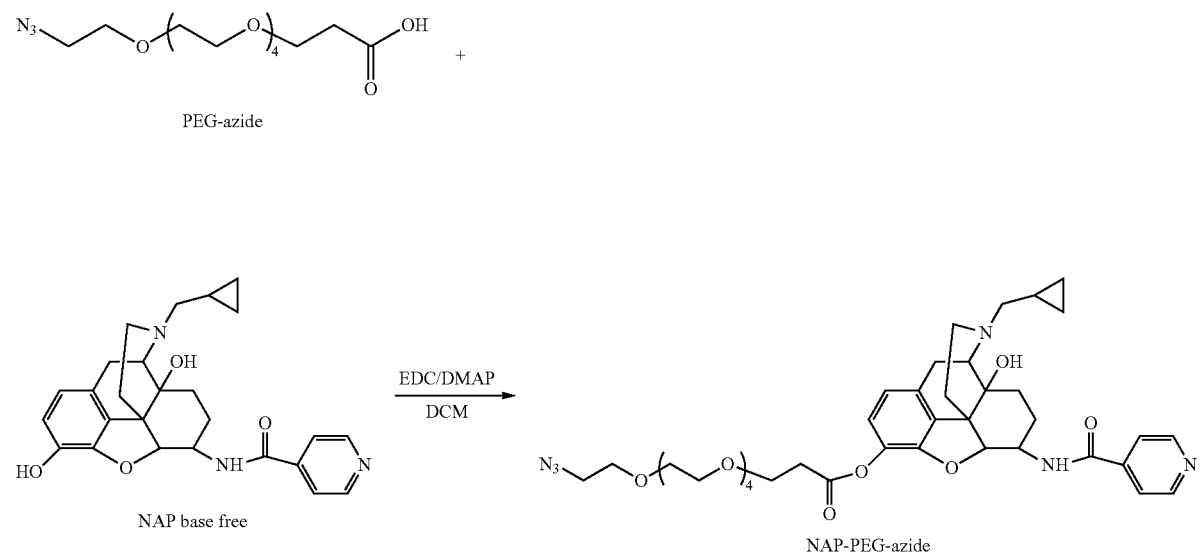

-continued

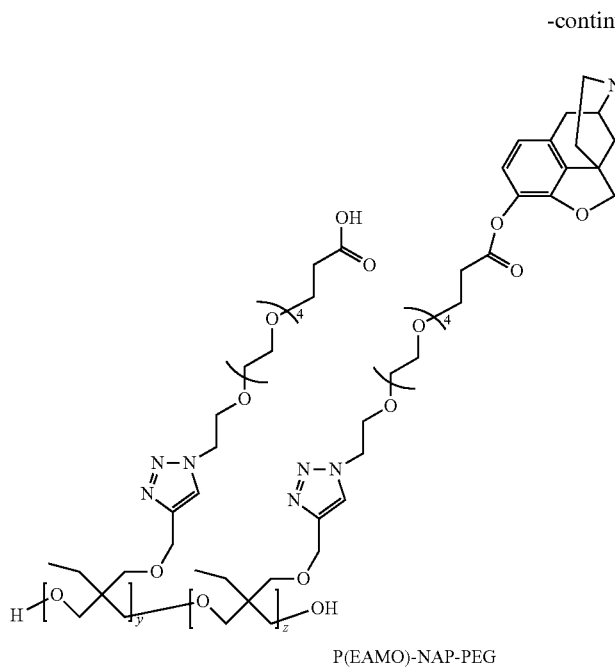

P(EAMO)-NAP-PEG

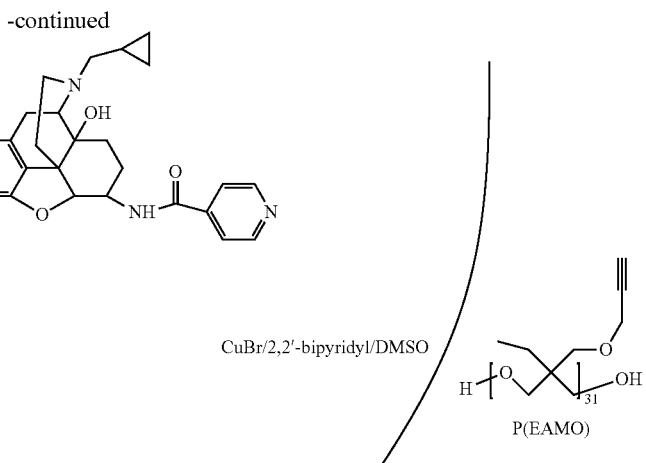

P(EAMO)

Characterization

Figure 2:
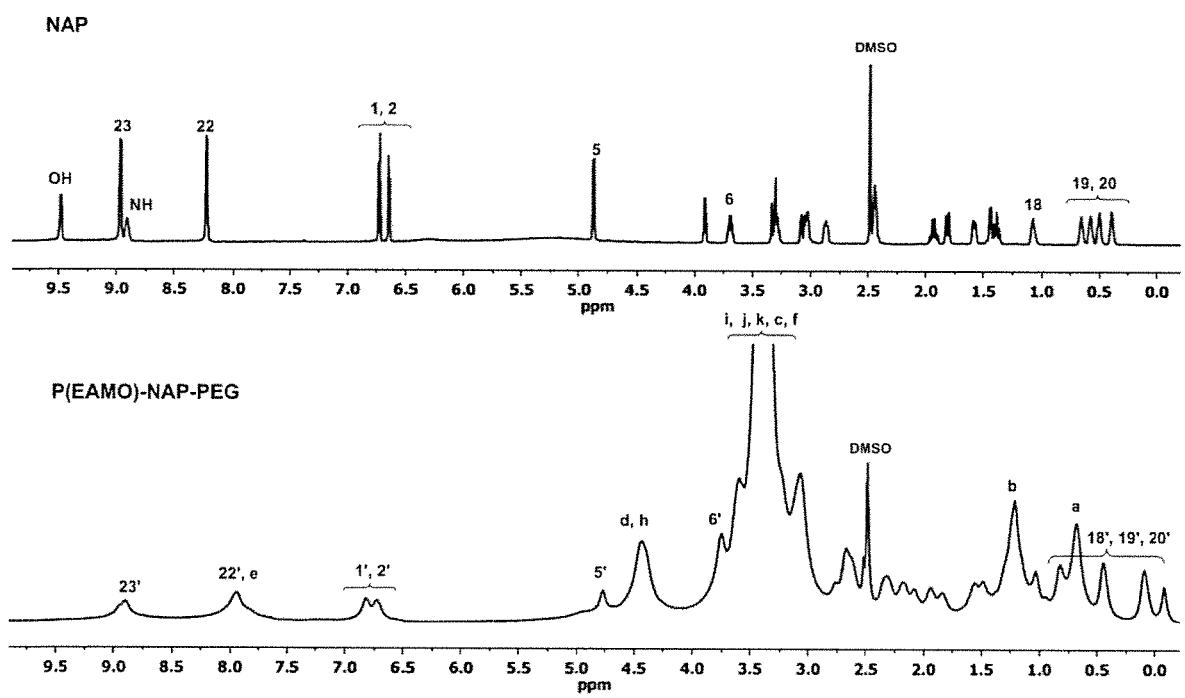
FIG. 2. NMR spectra of NAP and P(EAMO)-NAP-PEG in $d_6$-DMSO.
Figure 3:
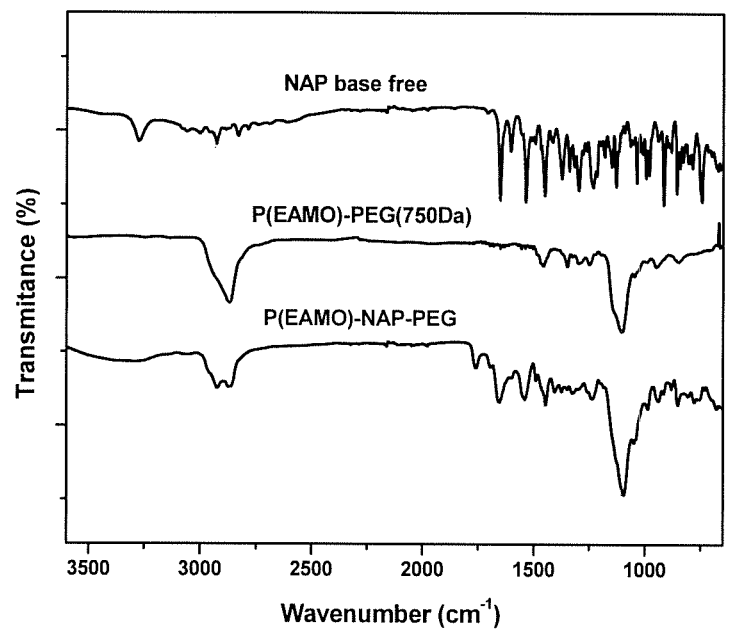
FIG. 3. FTIR spectra of NAP free base, P(EAMO)-PEG (750 Da), and P(EAMO)-NAP-PEG.

P(EAMO)-NAP-PEG was characterized by $^1$HNMR (FIG. 2) and IR (FIG. 3). $^1$HNMR: (DMSO-d$_6$, 600 MHz): δ (ppm) 8.87 (br, s, 2H), 7.93 (br, s, 3H), 6.76 (d, 2H), 4.76 (s, 1H), 4.43 (br, s, 4H), 4.10-2.00 (m, 37H), 1.92-0.9 (m, 5H), 1.20 (br, s, 2H), 0.67 (s, 3H), 0.85-0.2 (m, 6H). IR v$_{max}$ (neat) cm$^{-1}$: 2922, 2853, 1653, 1539, 1444, 1229, 1091.

Critical Micelle Concentration (CMC) Determination

The pyrene I1/I3 ratio method (Frindi, et al. J. Phys. Chem. 1992, 96, 8137-41) was applied to determine critical micelle concentration of nanoconjugated NAP. A series of NAP nanoparticle solutions from 1 mg/L up to 5 g/L containing 0.6 µM of pyrene were prepared by dissolving appropriate amounts of nanoconjugated NAP in the pyrene water solution followed by heating at 65° C. for 3 h and equilibration at room temperature for 16 h. Fluorescent emission spectra of the pyrene-containing solutions were then recorded using an excitation wavelength of 335 nm. The intensities of I1 at the wavelength of 370 nm and I3 at the wavelength of 390 nm were measured and the ratio of I1/I3 against NAP nanoconjugate concentration was plotted.

Particle Size and Zeta Potential Measurements

PBS was filtered through a 20 nm filter. The size and zeta potential of nanoconjugated NAP at concentration above CMC were measured at room temperature using a Malvern Zetasizer Nano ZS90 apparatus (Malvern Instruments, Worcestershire, U.K.).

In Vitro Competitive Radioligand Binding and Functional Assays

The radioligand binding and the [$^{35}$S]GTPγS binding assays were conducted using monocloned opioid receptor-expressed Chinese hamster ovarian (CHO) cell lines as described previously (Li, et al. J Med Chem 2009, 52, 1416-27). Briefly, for the competition binding assay, [$^3$H] naloxone, [$^3$H]diprenorphine, and [$^3$H]naltrindole were used to label the opioid receptors (ORs) MOR, kappa OR (KOR), and delta OR (DOR), respectively. Aliquots of a membrane protein (30 µg) were incubated with the corresponding radioligand in the presence of seven different concentrations of the ligand under investigation in TME buffer (50 mM Tris, 3 mM MgCl$_2$, 0.2 mM EGTA, pH 7.7) at 30° C. for 1.5 h. The bound radioactive ligand was separated from the free radioligand by filtration using the Brandel harvester (Biomedical Research & Development Laboratories, MD).

Specific (i.e., opioid receptor-related) binding was determined as the difference in binding obtained in the absence and presence of 5 M naltrexone, 5 µM U50,488, and 5 M SNC80 for MOR, KOR, and DOR, respectively. The potency of a drug in displacing the specific binding of the radioligand was determined by linear regression analysis of Hill plots. IC$_{50}$ values were then determined and converted to K$_i$ values using the Cheng-Prusoff equation. MOR [$^{35}$S] GTPγS functional assays were conducted in the same cell membranes used in the receptor binding assays. Membrane proteins (10 µg) were incubated with varying concentrations of compounds, GDP (10 µM) and 0.1 nM [$^{35}$S]GTPγS in assay buffer (50 mM Tris, 3 mM MgCl$_2$, 100 mM NaCl, 0.2 mM EGTA, pH 7.7) for 1.5 h at 30° C. Nonspecific binding was determined with 20 µM unlabeled GTPγS. [D-Ala2, N-Me-Phe4, Gly5-ol]-Enkephalin (DAMGO) (3 µM) was included in the assay for a maximal effect of a full agonist for MOR.

In Vivo Activity Studies

P(EAMO)-NAP-PEG was dissolved in DMSO and then diluted to the desired concentration such that the DMSO concentration did not rise above ten percent.

Tail Immersion Test. The warm water tail-immersion test was performed according to previously described methods using a water bath with the temperature maintained at 56±0.1° C.[4] Briefly, before giving the mice injections, a baseline (control) latency was determined. Only mice with a control reaction time of 2 to 4 s were used. The test latency after drug treatment was assessed at the appropriate time, and a 10 s maximal cutoff time was imposed to prevent tissue damage. Antinociception was quantified according to established procedures as the percentage of maximum possible effect (% MPE), which was calculated as follows: %

MPE=[(test latency−control latency)/(10−control latency)]× 100.[5] Percentage MPE was calculated for each mouse, using at least six mice per group.

Charcoal Meal Test for Gastrointestinal Transit Analysis. Forty-eight hours before testing, mice were placed in cages with raised mesh wire to suspend them above their bedding and prevent ingestion of feces or bedding. The animals were habituated for 24 h in the presence of food and water and then fasted for 24 h with free access to water as previously reported (Raehal, et al. J. Pharmacol. Exp. Ther. 2005, 314, 1195-201). This time frame was chosen to deplete the intestine and colon of any feces. To maintain caloric intake and to avoid hypoglycemia, mice had access to a sugar water solution consisting of a final concentration of 5% dextrose for the first 8 h of the fasting period. In control experiments mice were treated with either saline (10 g/g s.c.) or morphine (2 mg/kg s.c.), and 20 min later they were given an oral gavage consisting of 5% aqueous suspension of charcoal in a 10% gum Arabic solution. At 30 min after the administration of the charcoal meal, the mice were euthanized by cervical dislocation, and the small intestine from the jejunum to the cecum was dissected and placed in cold saline to stop peristalsis. The distance traveled by the leading edge of the charcoal meal was measured relative to the total length of the small intestine, and the percentage of intestinal transit for each animal was calculated as percentage transit (charcoal distance)/(small intestinal length)×100. This was referred to as intestinal transit in the text. In drug treated mice, mice were treated with P(EAMO)-NAP-PEG either by subcutaneous injection or through oral gavage 15 min prior to the administration of either saline (10 l/g s.c.) or morphine (2 mg/kg s.c.). 20 min following this, mice were then given an oral gavage consisting of 5% aqueous suspension of charcoal in a 10% gum Arabic solution. At 30 min past administration of the charcoal meal, the mice were euthanized by cervical dislocation, and the small intestine from the jejunum to the cecum was dissected and placed in cold saline to stop peristalsis. The percentage of intestinal transit for each animal was calculated as described above.

Results

Ideally, nanoparticles would have the advantages of high load ability and improved periphery selectivity. As described above, NAP-PEG-azide was synthesized by coupling NAP to PEG-azide via a Steglich esterification. A click reaction between NAP-PEG-azide and P(EAMO) furnished the synthesis of NAP nanoconjugates. For an NMR analysis, a singlet 7.94 ppm (FIG. 2) was assigned to a proton of the triazole ring, indicating the success of the click reaction. The $^1$H NMR spectrum also indicated that no free NAP was present in the nanoconjugates (FIG. 2). The FTIR spectrum of nanoconjugated NAP (FIG. 3) clearly presented absorption carried over from NAP and P(EAMO)-PEG, respectively. The vanishing of a weak alkyne absorption peak at 2108 cm$^{-1}$ in nanoconjugated NAP further confirmed a 100% substitution. According to $^1$H NMR spectroscopy analysis, 73% of NAP in the crude intermediate was conjugated to P(EAMO) through PEG. Combined analysis indicated that all alkynes were click coupled with PEG moieties, out of which 19 repeat units contained the drug. The conjugated NAP formula was defined as P(EAMO)-(PEG-Acid)$_{12}$-(PEG-NAP)$_{19}$.

Figure 4:
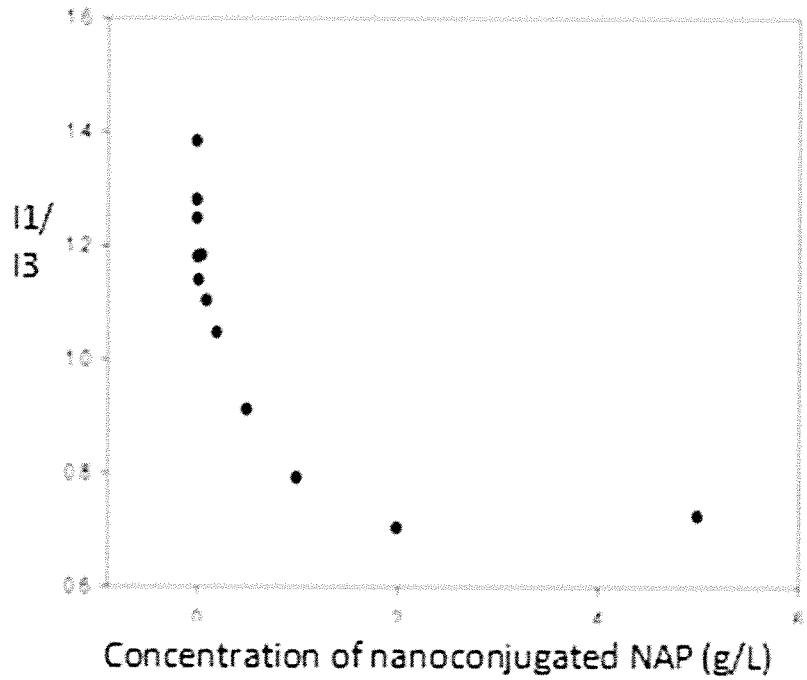
FIG. 4. Critical micelle concentration evaluation. Plot of pyrene I1/I3 ratio versus concentration of nanoconjugated NAP.

The synthesized NAP nanoparticle was then evaluated for its critical micelle concentration (CMC). FIG. 4 presents the pyrene 11/13 ratio plot for nanoconjugated NAP in water. Using pyrene as a fluorescence probe, the CMC of nanoconjugated NAP was determined to be 0.95 g/L, after which nanoconjugated NAP forms stable micelles. Nanoconjugated NAP formed stable micelles with an average particle size of 541.5±89.3 nm and a zeta potential of 31.0±13.7 mV at concentrations above the CMC.

The nanoconjugated NAP was then evaluated for its binding activities at opioid receptors. The results are presented in Table 1. Compared to naltrexone (NTX) and the parent lead compound NAP, nanoconjugated NAP retained high binding affinity at the MOR with a $K_i$ of 1.76 nM (based on an average molecular weight of 23375 g/mol). The binding affinity of nanoconjugated NAP at the KOR was in fact higher than that of NAP itself. As a result, nanoconjugated NAP displayed a similar selectivity for MOR over KOR, when compared to NTX (Table 1). Nanoconjugated NAP only inhibited 18.27+/−1.35% [$^3$H]naltrindole binding to DOR at 10 μg/mL, the highest concentration that can be used to maintain a minimum percentage of DMSO in the assay. Because of concentration limitation, the IC$_{50}$ and $K_i$ values of nanoconjugated NAP at DOR could not be determined under the tested conditions. Therefore, an arbitrary IC$_{50}$ of >10 μg/mL was plugged into the Cheng-Prusoff equation to obtain a $K_i$ value to estimate its selectivity. Apparently nanoconjugated NAP still maintained NAP's high selectivity over the DOR (See Supporting Information for detailed protocols). The MORefficacy of nanoconjugated NAP was then evaluated using the MOR [35S]GTPγS binding assay. Similar to NAP, nanoconjugated NAP acted as a low-efficacy MOR partial agonist (25.1% Emax of DAMGO) (Table 1). Interestingly, nanoconjugated NAP showed the lowest potency in activating MOR (EC50=6.44±0.83 nM) compared to NTX and NAP. This is a desired characteristic for therapeutic purpose in order to reduce potential side effect related to activation of the MOR.

TABLE 1

Binding affinity, selectivity and efficacy of nanoconjugated NAP[a]

| Compound | $K_i$ (nM) | | | Selectivity | | MOR [$^{35}$S]GTPγS Binding | |
|---|---|---|---|---|---|---|---|
| | μ | κ | δ | κ/μ | δ/μ | EC$_{50}$ (nM) | % E$_{max}$ of DAMGO |
| NAP[b] | 0.39 ± 0.04 | 4.3 ± 1.1 | 127.8 ± 3.5 | 11 | 328 | 0.16 ± 0.04 | 5.4 ± 0.8 |
| | 0.37 ± 0.07 | 60.7 ± 5.6 | 277.5 ± 8.0 | 164 | 750 | 1.14 ± 0.38 | 22.7 ± 0.8 |
| NC-NAP | 1.76 ± 0.28 | 22.6 ± 2.6 | —[c] | 13 | >64[d] | 6.44 ± 0.83 | 25.1 ± 1.0 |

[a]The values are the means ± S.E.M. of at least three independent experiments. [$^3$H]naloxone, [$^3$H]diprenorphine, and [$^3$H]naltrindole were used to label MOR, KOR and DOR, respectively. The percentage stimulation to DAMGO is the E$_{max}$ of the compound compared to that of DAMGO (normalized to 100%). NTX (naltrexone) was tested under the same conditions.
[b]Data taken from previously published results (Li, et al. J. Med. Chem. 2009, 52, 1416-27).
[c]Nanoconjugated NAP (NC-NAP) showed only 18.27 ± 1.35% inhibition of [$^3$H]naltrindole binding at 10 μg/mL (the highest concentration used in the assay).
[d]An arbitrary IC$_{50}$ of >10 μg/mL was used in the Cheng-Prusoff equation to obtain a $K_i$ value for the selectivity calculation.

Figure 5:
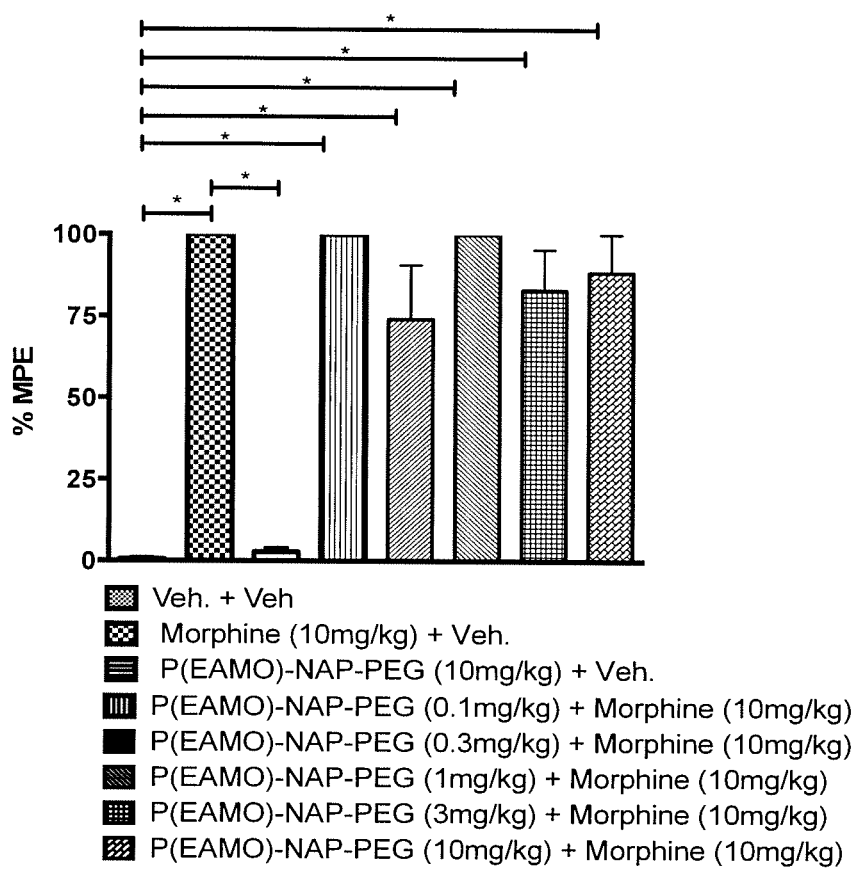
FIG. 5. Antinociceptive effects of morphine in the presence of P(EAMO)-NAP-PEG as measured in the warm water tail immersion test. Data points are mean responses S.E.M, n=4~5, *P<0.05

To investigate the peripheral selectivity of P(EAMO)-NAP-PEG, the warm water tail immersion test was performed in mice acutely treated with morphine (10 mg/kg) and P(EAMO)-NAP-PEG at increasing concentrations from 0.1 mg/kg to 10 mg/kg (FIG. 5). P(EAMO)-NAP-PEG alone at the maximum dose of 10 mg/kg did not show any antinociceptive effects. Importantly P(EAMO)-NAP-PEG did not antagonize morphine antinociception at doses up to 10 mg/kg. As the formula of nanoconjugated NAP was defined as P(EAMO)-(PEG-Acid)$_{12}$-(PEG-NAP)$_{19}$, the dose range of P(EAMO)-NAP-PEG (0.1 to 10 mg/kg) can be calculated as 0.037 to 3.7 mg/kg with respect to NAP. Due to solubility considerations, a higher dose than 10 mg/kg was not be tested. It is noted that NAP, the parent compound, though it did not carry any significant agonist activity, did show a certain degree of antagonist activity in the CNS and blocked the antinociceptive effect of morphine (AD$_{50}$ at 4.98 mg/kg). The advantageously diminished CNS activity of nanoconjugated NAP compared to NAP indicated that the nanoparticle skeleton (i.e. the polymer carrier) further reinforced the peripheral selectivity of NAP, serving as a proof-of-concept for future drug development.

Figure 6A:
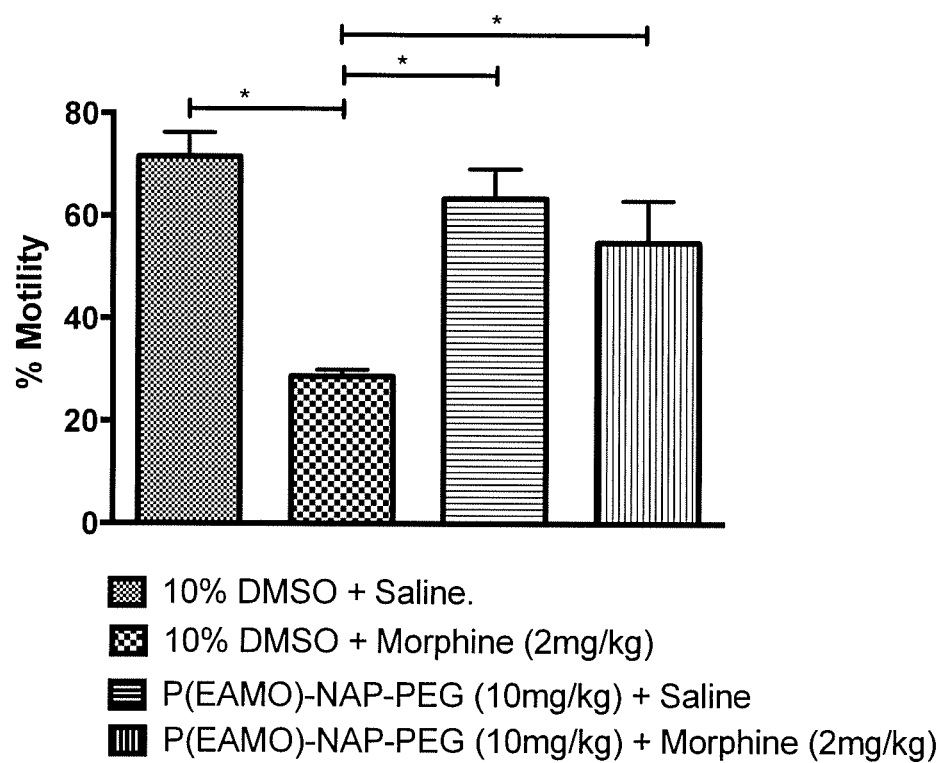
FIGS. 6A and B. P(EAMO)-NAP-PEG effects on intestinal motility in acute morphine treated mice. (A) subcutaneous (s.c.) injection of P(EAMO)-NAP-PEG; (B) Oral administration of P(EAMO)-NAP-PEG. Data points are mean responses S.E.M n=4-9, *P<0.05.
Figure 6B:
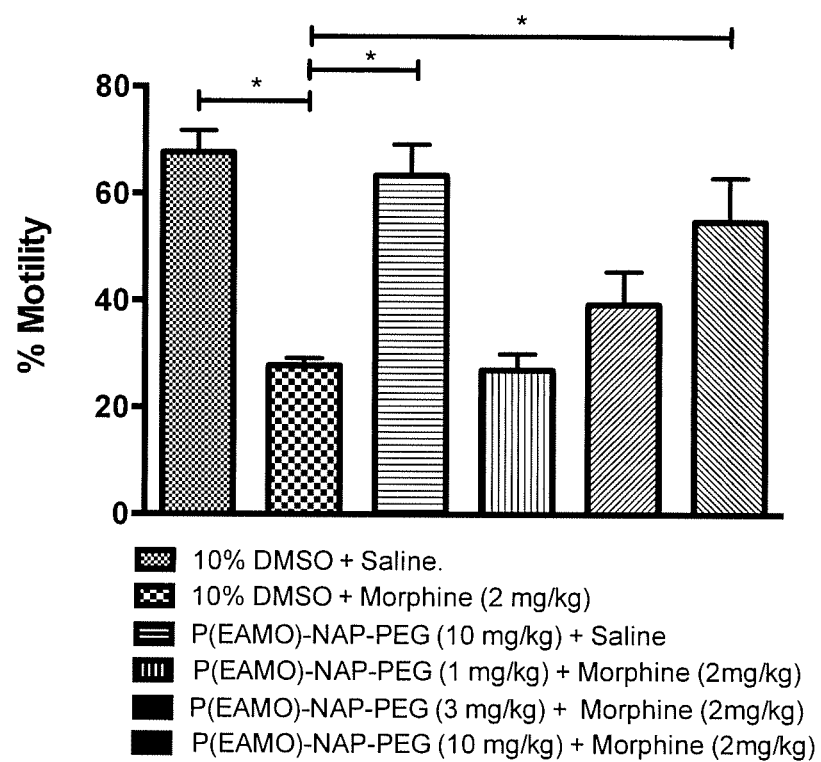

It is well known that morphine significantly reduces GI motility. Given the diminished CNS activity of P(EAMO)-NAP-PEG as observed in the tail flick test, P(EAMO)-NAP-PEG was examined for its activity in the GI transit. The results showed that P(EAMO)-NAP-PEG alone exhibited no effect on GI motility when compared to vehicle treated groups. When administered via subcutaneous (s.c.) injection, P(EAMO)-NAP-PEG showed a degree of reversal of morphine's effects on GI transit at the maximum dose used of 10 mg/kg (FIG. 6A), but no dose response was observed (data not shown). On the other hand, when given via oral gavage, P(EAMO)-NAP-PEG did show a dose dependent reversal of morphine effects on GI motility and the highest reversal occurred at 10 mg/kg (ED$_{50}$=4.1±2.9 mg/kg, FIG. 6B).

In summary, nanoconjugated NAP was synthesized using a P(EAMO) carrier via the click reaction between the alkyne and azide, and was characterized and structurally confirmed through $^1$H NMR and FTIR. The NAP nanoparticles formed micelles over a concentration of 0.95 g/L, with an average particle size of 541.5±89.3 nm and a zeta potential of 31.0±13.7

In in vitro and in vivo biological studies, the NAP nanoconjugates remained individual entities given that the concentration of nanoconjugated NAP was well below its CMC. Nanoconjugated NAP was shown to be a potent and selective MOR agent. Nanoconjugated NAP maintained the ability to treat opioid induced constipation with a surprising improved periphery selectivity over NAP, the parent lead compound. These results show that nanotechnology applications in drug delivery system are very useful in medication development.

Prodrugs other than NAP nanoconjugates are synthesized by procedures that are substantially the same as those described above for P(EAMO)-NAP-PEG, except that differing reaction times may be necessary to complete each reaction step.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound having the general formula:

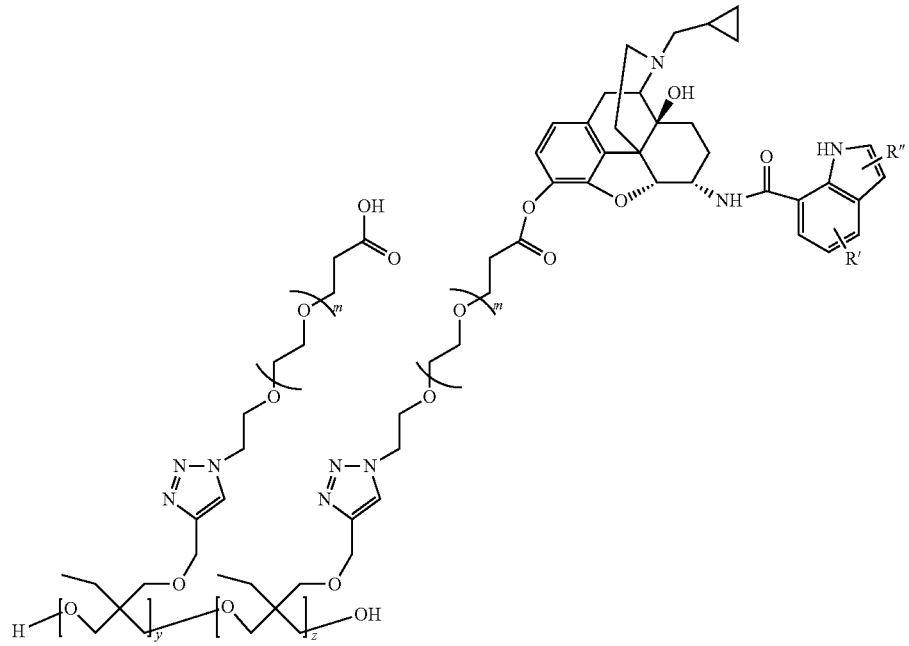

where
m=0-16;
y=5-20;
z=10-30; and
R' and R" are independently hydrogen or a substituted or unsubstituted aromatic or aliphatic moiety.

2. The compound of claim 1, wherein the compound is

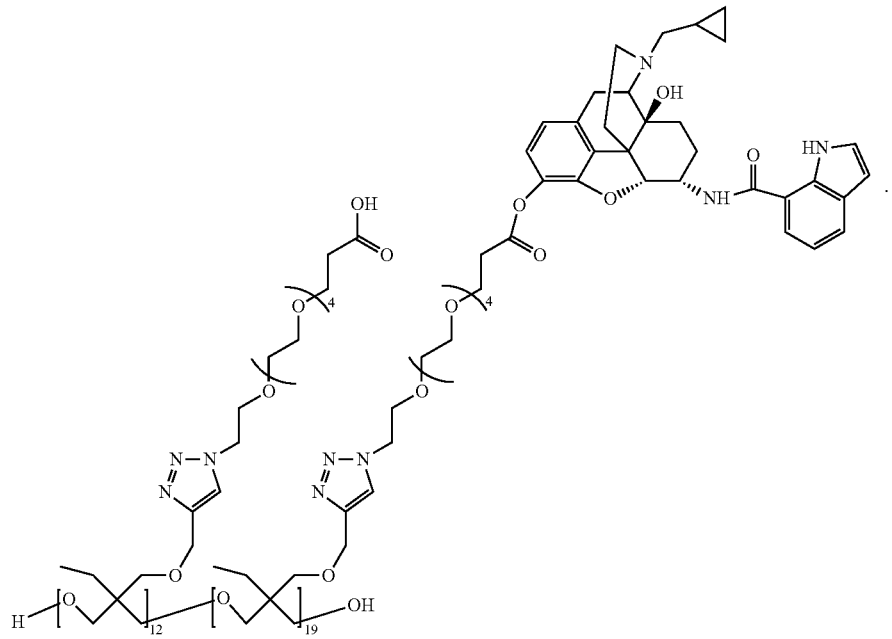

3. A method of preventing or treating opioid induced constipation (OIC) in a subject in need thereof, comprising administering to the subject a therapeutically effective amount of a compound having the general formula

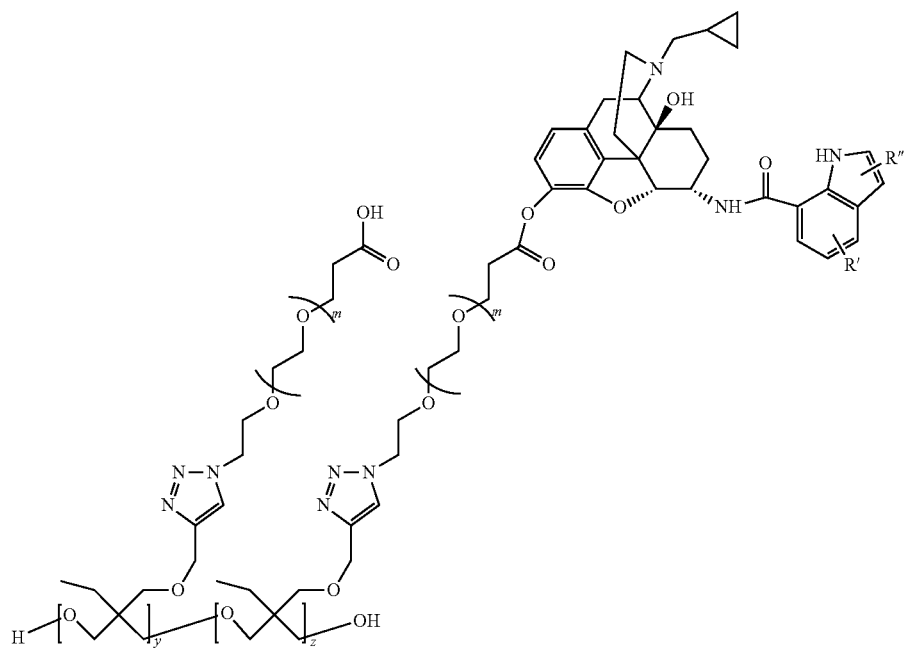

where
m=0-16;
y=5-20;
z=10-30; and
R' and R" are independently hydrogen or a substituted or unsubstituted aromatic or aliphatic moiety.
4. The method of claim 2, wherein the compound is
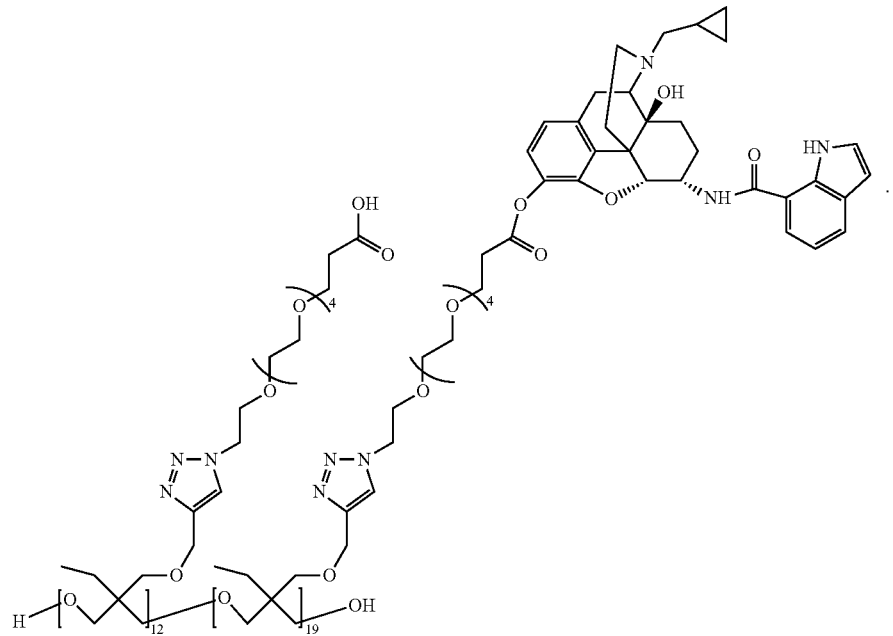
* * * * *